(12) United States Patent
Michael et al.

(10) Patent No.: US 11,370,757 B2
(45) Date of Patent: Jun. 28, 2022

(54) PHOTOCLEAVABLE NITROINDOLINE-BASED CROSSLINKERS

(71) Applicant: Board of Regents, The University of Texas System, Austin, TX (US)

(72) Inventors: Katja Michael, El Paso, TX (US);
Chunqlang Li, El Paso, TX (US);
Thomas Boland, El Paso, TX (US);
Hector P. Del Castillo, El Paso, TX (US);
Binata Joddar, El Paso, TX (US);
Alfredo Ornelas Sanchez, El Paso, TX (US);
Javier Hernandez Ortega, El Paso, TX (US);
Irodiel Vinales Lozano, El Paso, TX (US);
Philip T. Baily, El Paso, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 17/074,232

(22) Filed: Oct. 19, 2020

(65) Prior Publication Data

US 2021/0130294 A1 May 6, 2021

Related U.S. Application Data

(63) Continuation-in-part of application No. 16/164,101, filed on Oct. 18, 2018, now abandoned.

(60) Provisional application No. 62/573,980, filed on Oct. 18, 2017.

(51) Int. Cl.
| | | |
|---|---|---|
| *C07D 209/08* | (2006.01) | |
| *C07H 15/26* | (2006.01) | |
| *C07D 403/12* | (2006.01) | |
| *C07D 405/12* | (2006.01) | |

(52) U.S. Cl.
CPC ......... *C07D 209/08* (2013.01); *C07D 403/12* (2013.01); *C07D 405/12* (2013.01); *C07H 15/26* (2013.01)

(58) Field of Classification Search
CPC .. C07D 209/08; C07D 403/12; C07D 405/12; C07H 15/26
See application file for complete search history.

(56) References Cited

U.S. PATENT DOCUMENTS

| 6,150,375 A * | 11/2000 | Audia ........................ A61P 5/28 |
| | | 514/290 |
| 2007/0203099 A1* | 8/2007 | Corrie ................... C07D 209/48 |
| | | 514/80 |
| 2010/0096252 A1* | 4/2010 | Ellis-Davies ......... C07F 9/5728 |
| | | 204/157.72 |

FOREIGN PATENT DOCUMENTS

| WO | WO-0055133 A1 * | 9/2000 | ................ A61P 5/06 |
| WO | WO-02070469 A2 * | 9/2002 | ........... C07D 333/18 |
| WO | WO-02083639 A1 * | 10/2002 | ........... C07D 209/08 |

OTHER PUBLICATIONS

Hawley's Condensed Chemical Dictionary, p. 265 (16th ed., 2016, R.J. Larrañaga ed.) (Year: 2016).*
K. C. Nicolaou et al., Synlett, 900-903 (2001) (Year: 2001).*
S Chakrabarty et al., 27 Cell Chemical Biology, 1434-1440 (Published Aug. 18, 2020) (Year: 2020).*
Picard et al., 49 Chemical Communications, 10805-10807 (2013) (Year: 2013).*
Polypropylene, Encyclopedia Britannica (2017), (Downloaded from https://www.britannica.com/print/article/469069) (Year: 2017).*
CAS Abstract and Indexed Compounds, S. Picard et al., 49 Chemical Communications, 10805-10807 (2013) (Year: 2013).*
CAS Abstract and Indexed Compounds S Chakrabarty et al., 27 Cell Chemical Biology, 1434-1440 (Aug. 18, 2020) (Year: 2020).*
B. Amit et al., 98 Journal of the American Chemical Society, 843-844 (1976) (Year: 1976).*
Achilli & Mantovani, "Tailoring Mechanical Properties of Collagen-Based Scaffolds for Vascular Tissue Engineering: The Effects of pH, Temperature and Ionic Strength on Gelation," Polymers, 2(4), 664 680, 2010.
Acosta, et al., "Imaging Cytosolic Translocation of*Mycobacteria* with Two-Photon Fluorescence Resonance Energy Transfer Microscopy," Biomedical Optics Express, 5(11), 3990-4001, 2014.
Agren,(Ed.), "Wound Healing Biomaterials," (2016) Functional Biomaterials, vol. 2, First Edition, Elsevier Ltd., Amsterdam, 2016.
Amit, "Light-Sensitive Amides. The Photosolvolysis of Substituted I-Acyl-7-Nitroindolines," Journal of the American Chemical Society, 98(3), 843-844, 1976.
Berthiaume, et al., "Effect of Extracellular Matrix Topology on Cell Structure, Function, and Physiological Responsiveness: Hepatocytes Cultured in a Sandwich Configuration," FASEB Journal, 10(13), 1471-1484, 1996.
Chan and White, (Eds ), "Fmoc Solid Phase Peptide Synthesis: A Practical Approach," vol. 222, Oxford University Press, Oxford, 2000.
Chapman and Walker, "Amino Acods and Peptides. Preparation and Reactions of a Polymer Diazomethylene," (1975) Journal of the Chemical Society, Chemical Communications, 16; 690- 91, 1975.
Cohen, et al., The Mechanism of Photoinduced Acylation of Amines by N-Acyl-5, 7-Dinitroindoline as Determined by the Time-Resolved Infrared Spectroscopy, Organic Letters, 7(14), 2845-48, 2005.
Debieux & Bochet, "Preparation of Photoactivable Amino Acid Derivatives," The Journal of Organic Chemistry, 74(12), 2073-2077,2009.

(Continued)

*Primary Examiner* — Alexander R Pagano
(74) *Attorney, Agent, or Firm* — Yee & Associates, P.C.

(57) ABSTRACT

Crosslinkers of an amide or thiocarbamate of 7-nitroindoline were prepared with at least two attached reactive groups for crosslinking capability. The photo-cleavability of the invented crosslinkers is based on the known photolysis behavior of N-acyl-7-nitroindolines, and the photolysis behavior of amides and thiocarbamates of 7-nitroindolines. These crosslinkers enable crosslinking of biopolymers, which can be reversed by illumination with light.

1 Claim, 12 Drawing Sheets

(56) References Cited

OTHER PUBLICATIONS

Du, et al., "Convergent Synthesis ofN-Linked Glycopeptides via Aminolysis of co Asp P-Nitrophenyl Thioesters in Solution," Organic Letters, 18; 4828-4831, 2016.
Ellis-Davies, "Caged Compounds : Photorelease Technology for Control of Cellular Chemistry and Physiology," Nature Methods, 4(8), 619-28, 2007.
Farsari and Chichkov, "Two-Photon Fabrication," Nature Photonics, 3(8), 450-52, 2009.
Frank, "Stabilization of Short Collagen-Like Triple Helices by Protein Engineering," Journal of Molecular Biology, 308 (5), 1081-89, 2001.
Frantz, "The Extracellular Matrix at a Glance," Journal of Cell Science, 123(24), 4195-4200, 2010.
Gopal, et al., "Applications of Circular Dichroism for Structural Analysis of Gelatin and Antimicrobial Peptides," International Journal of Molecular Sciences, 13(3), 3229-3244, 2012.
Han & Gouma, "Electrospun Bioscaffolds That Mimic the Topology of Extracellular Matrix," Nanomedicine: Nanotechnology, Biology and Medicine, 2(1), 37-41, 2006.
Hassner, et al., Light-Sensitive Protecting Groups for Amines and Alcohols: The PhotoSolvolysis ofN-Substituted 7-Nitroindolines, Synlett, 2405-2509, 2007.
Hatch, et al., "Photolysis of a Peptide with N-Peptidyl-7-Nitroindoline Units Using Two-Photon Absorption," (2016) Biomedical Optics Express, 7(11), 4654-59, 2016.
Helgen and Bochet, "Photochemical Protection of Amines with Cbz and Fmoc Groups," Journal of Organic Chemistry, 68(6), 2483-86, 2003.
Hernandez-Gordillo & Chmielewski, "Mimicking the Extracellular Matrix with Functionalized, Metal-Assembled Collager Peptide Scaffolds," Biomaterials, 35(26), 7363-7373, 2014.
Herrmann, "Using Photolabile Protecting Groups for the Controlled Release of Bioactive Volatiles," Photochemical & Photobiological Sciences II(3), 446-59, 2012.
Hogenauer, et al., "Virtually Epimerization-Free Synthesis of Peptide-a-thioesters," Organic & Biomolecular Chemistry, 5, 759-62, 2007.
Joddar, et al., "Spatial Gradients of Chemotropic Factors from Immobilized Patters to Guide Axonal Growth and Regeneration," Biomaterials 34(37), 9593-9601, 2013.
Kaneshiro and Michael, "A Convergent Synthesis ofN-Glycopeptides," Angewandte Chemie International. Edition, 45 (7), 1077-1081, 2006.
Klan, et al., "Photoremovable Protecting Groups in Chemistry and Biology: Reaction Mechanisms and Efficacy," Chemical Reviews 113(1), 119-191, 2013.
Koide, "Designed Triple-Helical Peptides as Tools for Collagen Biochemistry and Matrix Engineering," Philosophical Transactions of the Royal Society B, 362, 1281-91, 2007.
C27 Kotch and Raines, "Self-Assembly of Synthetic Collagen Triple Helices," PNAS, 103(9), 3028-3033, 2006.
Langelaan, et al., "Biophysical Characterization of G-Protein Coupled Receptor-Peptide Ligand Binding," Biochemistry Cell Biology, 89(2); 98-105, 2011.
Leikina et al., "Type 1 Collagen is Thermally Unstable at Body Temperature," PNAS, 99(3), 1314-1318, 2002.
Li and Zheng, "Photoactivatable Fluorophores and Techniques for Biological Imaging Applications," Photochemical & Photobiological Sciences 11(3), 460-71, 2012.
Li, et al., "Photoinduced Electron Transfer in Folic Acid Investigated by Ultrafast Infrared Spectroscopy," Journal of Physical Chemistry B, 116; 3467-3475, 2012.
Li, and Yu, Targeting and Mimicking Collagens Via Triple Helical Peptide Assembly, Current Opinion in Chemical Biology, 17(6), 968-975, 2013.
Matsuzaki, et al., "Dendritic Spine Geometry is Critical for AMPA Receptor Expression in Hippocampal CAI Pyramidal Neurons," Nature Neuroscience, 4(11), 1086-92, 2001.
Mendez, et al., "Photoreactivity ofN-Acetyl-7-Nitroindolines-Unraveling the Mechanism by Computation," Trends in Photochemistry & Photobiology, 14, 75-91, 2012.
Morrison, "Mechanisms of Photorelease of Carboxylic Acids from 1-Acyl-7-Nritroindolines in Solutions of Varying Water Content," Photochemicals & Photobiological Sciences, 1, 960-69, 2002.
Nicolaou, et al., "A New Photolabile Linker for the Photoactivation of Carboxyl Groups," Synlett, 900-03, 2001.
Ornelas, et al.,, "Synthesis and Characterization of Photocleavable Collagen-Like Peptide," Organic and Biomolecular Chemistry, 16; 1000-1013, 2016.
Papageorgiou et al., "Photorelease of Carboxylic Acids from I-Acyl-7-Nitroindolines in Aqueous Solution: Rapid and Efficient Photorelease ofL-Glutamate," Journal of the American Chemical Society, 121(7), 6503-04, 1999.
Papageorgiou et al., "Synthetic and Photochemical Studies of Substituted I-Acyl-7-Nitroindolines," Photochemical & Photobiological Sciences 4, 887-896, 2005.
Pardo et al., "Efficient Photochemical Synthesis of Peptide-a-Phenylthioesters," ChemBioChem 16(13), 1884-1889, 2015.
Pass et al., "Racemization-Free Photochemical Coupling of Peptide Segments," Journal of the American Chemical Society, 103(25), 7674-7675, 1981.
Persikov et al., "Equilibrium Thermal Transitions of Collagen Model Peptides," Protein Science, 13(4), 893-902, 2004.
Raimondi, "Two-Photon Laser Polymerization: From Fundamentals to Biomedical Application in Tissue Engineering and Regenerative Medicine," Journal of Applied Biomaterials and Fundamental Materials, 10(1); 55-65, 2012.
Simo et al., "Synthesis of Glycosyl Amino Acids by Light-Induced Coupling of Photoreactive Amino Acids with Glycosylamines and 1-C-Aminomethyl Glycosides," Carbohydrate Research, 340(4), 557-566, 2005.
Vizvardi, et al., "Phototransamidation as a Method for the Synthesis of N-Glycosyl Asparagines," Chemical Letters, 32 (4), 348-49, 2003.
Yu, et al., "Collagen Mimetic Peptides: Progress Towards Functional Applications," Soft Matter, 7, 7927-7938, 2011.

\* cited by examiner

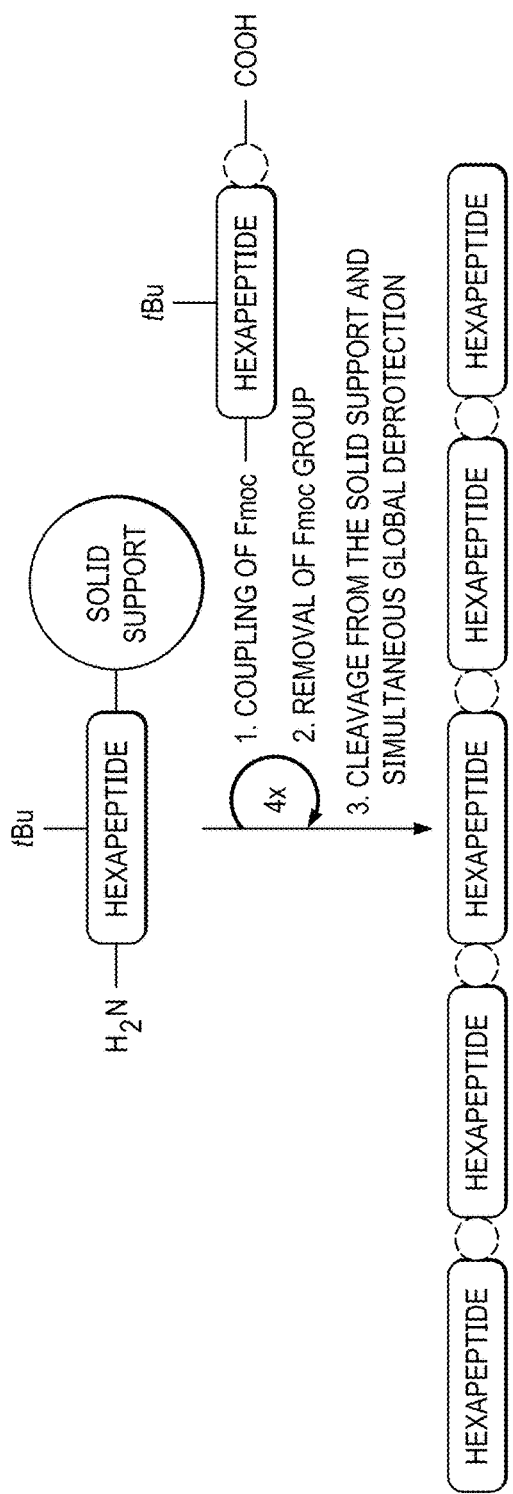
FIG. 2
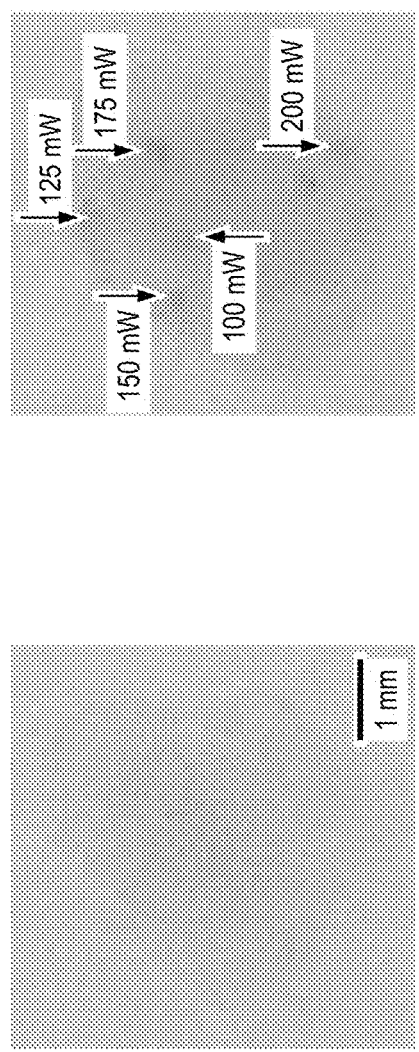
FIG. 3a
FIG. 3b

PHOTOCLEAVABLE NITROINDOLINE-BASED CROSSLINKERS

CROSS REFERENCE TO RELATED APPLICATIONS

This application a continuation-in-part of U.S. patent application Ser. No. 16/164,101, published as U.S. Patent Application Pub. No. 20190111132, which itself claims priority to Provisional Application No. 62/573,980 filed Oct. 18, 2017, both of which are incorporated herein by reference in its entirety.

STATEMENT REGARDING FEDERALLY FUNDED RESEARCH

This invention was made with government support under grant number DBI-1429708 awarded by the National Science Foundation; and grant numbers 1SC2GM103719, RL5GM118969, TL4GM118971, and UL1GM118970 awarded by the NIGMS National Institutes of Health. The government has certain rights in the invention.

BACKGROUND OF THE INVENTION

Collagen and collagen-derived materials have been used in tissue engineering applications, as these biomaterials form soft hydrogels that mimic the extracellular matrix (ECM) providing structural support in which cells can grow, differentiate, and proliferate. The extracellular matrix is geometrically and topologically inhomogeneous (Frantz et al., (2010) *J. Cell Sci.* 123, 4195-4200; Han and Gouma, (2006) *Nanomedicine* 2, 37-41), which are factors that modulate cell polarity and function (Berthiaume et al., (1996) *FASEB J.* 10, 1471-84). In the laboratory, collagen and gelatin can self-assemble in aqueous buffers resulting in gels consisting of protein fibrils that form a porous mesh microstructure. The size of the fibrils, the density of the mesh, and the mechanical properties can be controlled by varying the pH, temperature, and ionic strength at which the hydrogel is prepared (Achilli and Mantovani, (2010) *Polymers* 2, 664-80). However, the introduction of three-dimensional structural elements into a collagen-based hydrogel, e.g., pores of defined lengths and diameters at specific locations remains an unmet challenge.

SUMMARY OF THE INVENTION

The structural elements described above can be introduced if the macroscopic bulk material were composed of a peptide with unique properties that can be decomposed site-specifically into short, soluble peptide fragments. Described herein is a collagen-like peptide with incorporated photoreactive moieties can be photolytically decomposed at precise microscopic locations by illuminating specific location(s) within the macroscopic material.

Certain embodiments of the invention are directed to photoreactive peptides made from proteinogenic amino acids and photoreactive N-acyl-7-nitroindoline-containing amino acids, capable of photolytic cleavage with near ultraviolet light via a one-photon absorption process, or with infrared light via a multi-photon absorption process. The peptides can exist in solid forms or hydrogels, and the macroscopic material can be photolytically manipulated at the site of light illumination. The peptides can also be cross-linked, either naturally via disulfide bonds, or with commercially available cross-linkers, or with photoreactive N-acyl-7-nitroindoline-containing cross-linkers, lending mechanical stability to the hydrogel.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa.

The use of the word "a" or "an" when used in conjunction with the term "comprising" in the claims and/or the specification may mean "one," but it is also consistent with the meaning of "one or more," "at least one," and "one or more than one."

The terms "about" or "approximately" are defined as being close to as understood by one of ordinary skill in the art. In one non-limiting embodiment the terms are defined to be within 10%, preferably within 5%, more preferably within 1%, and most preferably within 0.5%.

The term "substantially" and its variations are defined to include ranges within 10%, within 5%, within 1%, or within 0.5%.

The terms "wt. %," "vol. %," or "mol. %" refers to a weight, volume, or molar percentage of a component, respectively, based on the total weight, the total volume, or the total moles of material that includes the component. In a non-limiting example, 10 moles of component in 100 moles of the material is 10 mol. % of component.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods of making and using the same of the present invention can "comprise," "consist essentially of," or "consist of" particular ingredients, components, blends, method steps, etc., disclosed throughout the specification.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

FIG. 2. Schematic of the assembly of a photoreactive polypeptide by on-resin fragment condensation. moieties=photoreactive N-peptidyl-7-nitroindoline; tBu=tert-butyl (permanent protecting group); Fmoc=flourenylmethyloxycarbonyl (temporary protecting group).

FIGS. 3A-B. Images of a sample of peptide 1 before (A) and after (B) irradiation at different laser powers, exhibiting formation of dark spots corresponding to photolysis products consisting of peptide fragments with 7-nitroindoline and/or 7-nitrosoindole covalently attached to them.

DETAILED DESCRIPTION OF THE INVENTION

A. Photoreactive Peptides

Figure 1A:
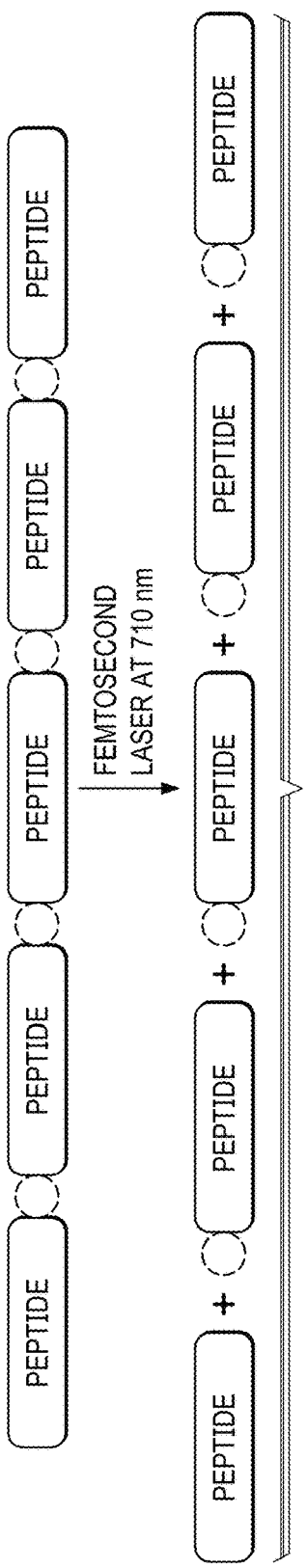
FIGS. 1A-B. (A) A polypeptide with built-in photoreactive moieties may undergo photolysis at all photoreactive sites when irradiated with a femtosecond laser at 710 nm. This photolysis generates a number of small peptide fragments; (B) Molecular structure of peptide 1: 34-mer peptide with four photoreactive N-peptidyl-7-nitroindoline units, which themselves can be regarded as amino acids.

Photoreactive peptides of Group I have a structure of Formula 1.

Formula I

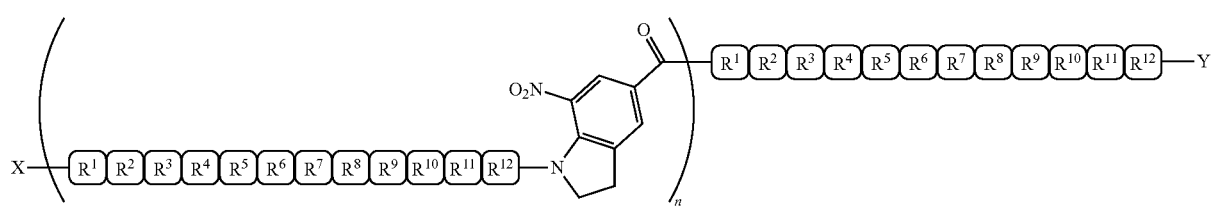

Formula I illustrates a photoreactive peptide having a first and second peptide moiety coupled to the nitroindoline containing photoreactive amino acid. In certain instance X—$R^1$-$R^{12}$ can be referred to a first peptide and $R^1$-$R^{12}$—Y can be referred to as a second peptide, each of which can have distinct sequences.

In certain aspects a peptide component can comprise one or more of $R^1$, $R^2$, $R^3$, $R^4$, $R^5$, $R^6$, $R^7$, $R^8$, $R^9$, $R^{10}$, $R^{11}$, $R^{12}$; where $R^1$-$R^{12}$ can be, independently, any proteinogenic amino acid (natural or non-natural amino acid) such as glycine, proline, alanine, serine, histidine, hydroxyproline, glutamic acid, phenylalanine, arginine, leucine, isoleucine, threonine, valine, etc. A proteinogenic amino acid comprises all natural and synthetic or non-natural amino acids that are not sufficiently susceptible to cleavage under the light exposure conditions described herein. The peptide component can include $R^1$-$R^{12}$, $R^2$-$R^{12}$, $R^3$-$R^{12}$, $R^4$-$R^{12}$, $R^5$-$R^{12}$, $R^6$-$R^{12}$, $R^7$-$R^{12}$, $R^8$-$R^{12}$, $R^9$-$R^{12}$, or $R^{10}$-$R^{12}$. In certain aspects the first and second peptides are the same or different peptides, with each peptide having the same or different lengths.

In certain aspects, $R^1$, $R^2$, $R^3$, $R^4$, $R^5$, $R^6$, $R^7$, $R^8$, and/or $R^9$ may not be present at all, indicating that the peptide sequences between nitroindoline moieties may have different lengths, i.e., between 3, 4, 5, 6, 7, 8, 9, 10, 11, or 12 amino acids. In certain aspects the first and second peptide have the same or different lengths.

In certain aspects, X can be acetyl (indicating a peptide with an amide-capped N-terminus) or H (indicating a peptide with a free N-terminus).

In certain aspects Y can be OH (indicating a peptide acid) or $NH_2$ (indicating a peptide amide).

In certain aspects n can be 1-20, indicating the peptide can vary in length with different numbers of repeating units, and different numbers of photoreactive N-peptidyl-7-nitroindoline units.

Photoreactive peptides of Group II have a structure as illustrated in Formula II.

Formula II

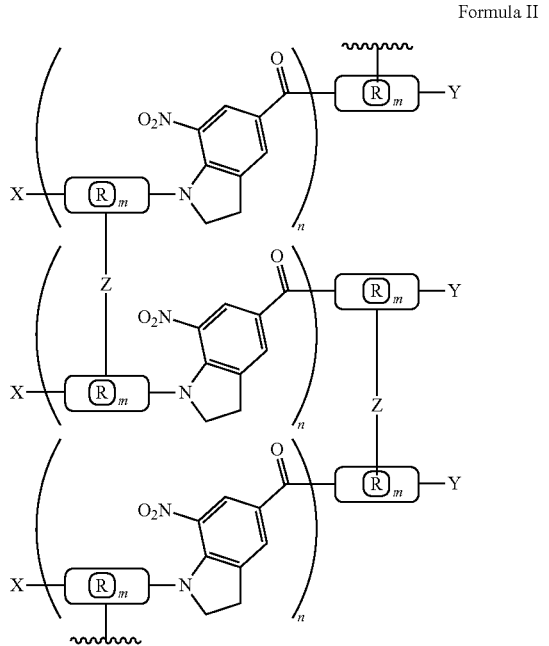

Photoreactive peptides of formula II can include various cross-links. In certain aspects the photoreactive peptides of Formula II are multimers of photoreactive peptides of Formula I.

In certain aspects, X can be acetyl (indicating a peptide with an amide-capped N-terminus) or H (indicating a peptide with a free N-terminus).

In certain aspects, Y can be —OH (indicating a peptide acid) or —$NH_2$ (indicating a peptide amide).

In certain aspects, n can be 1-20, indicating the peptide can vary in length with different numbers of repeating units, and different numbers of photoreactive N-peptidyl-7-nitroindoline units.

In certain aspects, R can be cysteine and/or lysine as one or more amino acids within the repeating peptide sequence, which is the same as in the Group I peptides. The side chain functionalities of cysteine and lysine are suitable for three-dimensional cross-linking between a large number of individual peptide strands.

In certain aspects, m can be 1, 2, or 3.

In certain aspects, Z can be introduced by one of the many commercially available homo- or heterobifunctional cross-linkers.

If R=cysteine, Z can also be

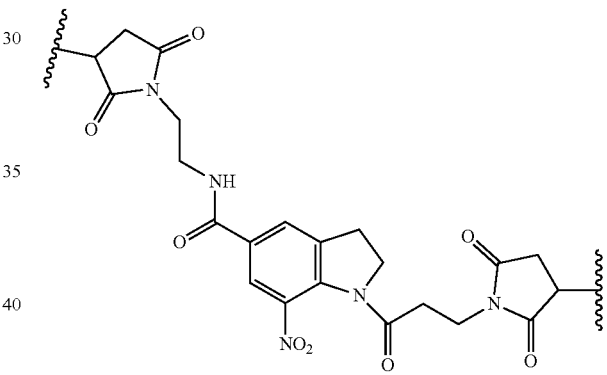

This linkage can be introduced between two thiols by the photoreactive homobifunctional cross-linker:

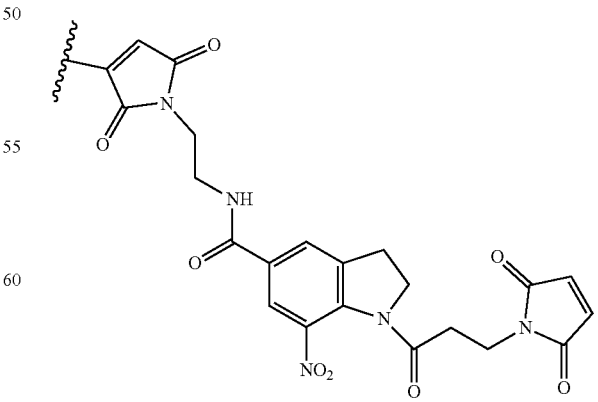

If R=lysine, Z can be:
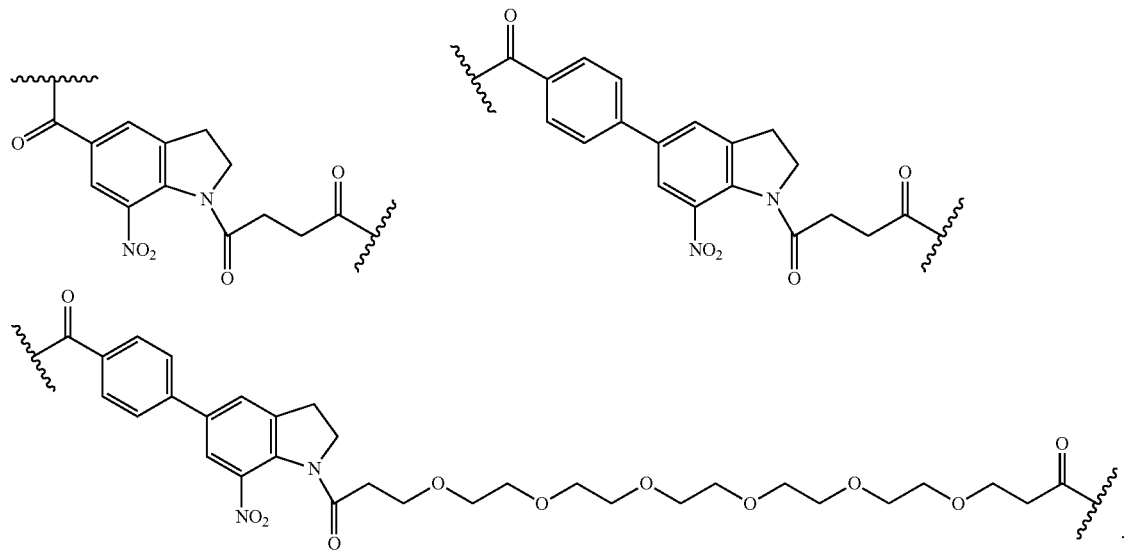
These linkages can be introduced between two primary amino groups by the photoreactive homobifunctional cross-linkers:
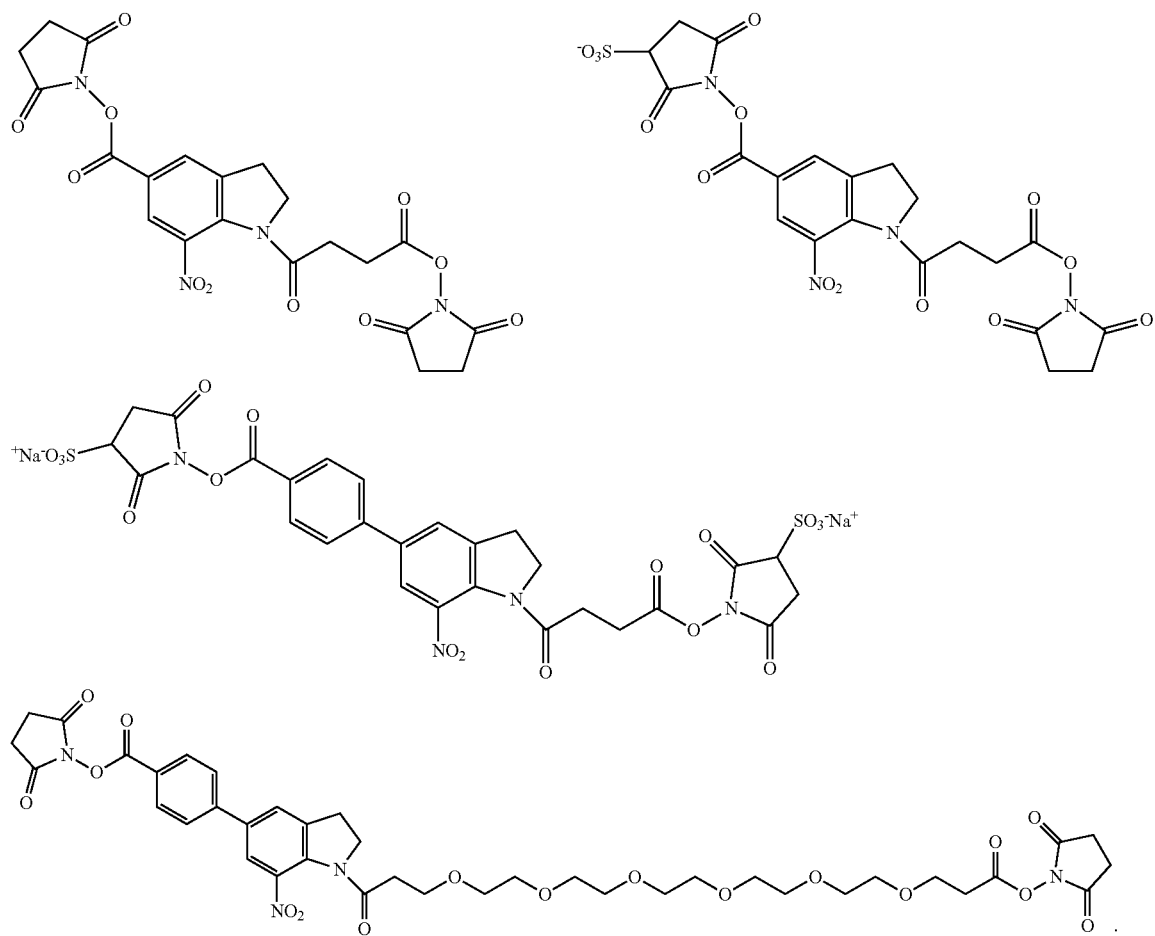

If R=a mixture of cysteine and lysine, Z can be:

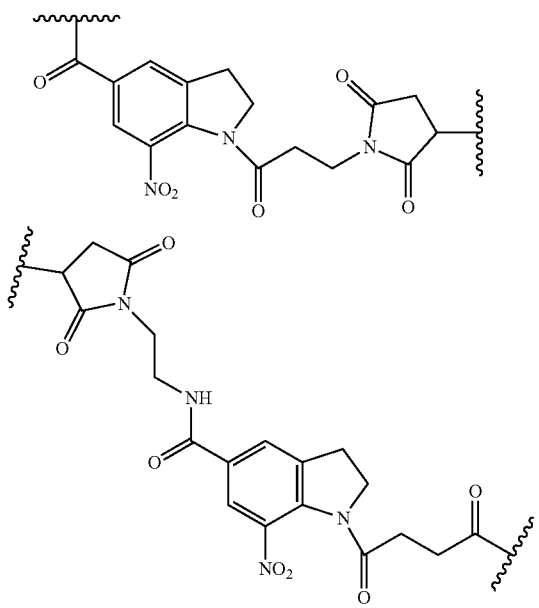

These linkages can be introduced between a primary amino group and a thiol group by the photoreactive heterobifunctional cross-linkers:

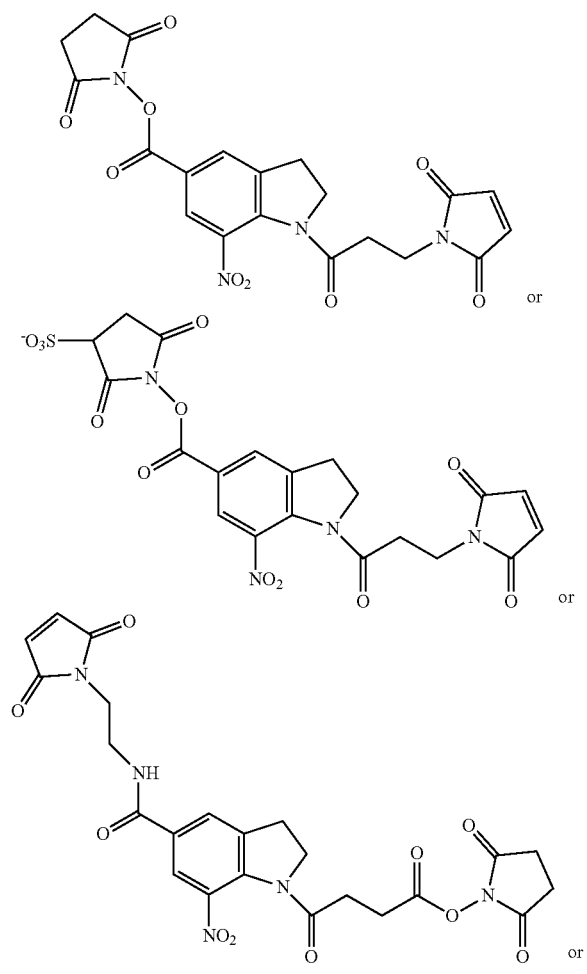

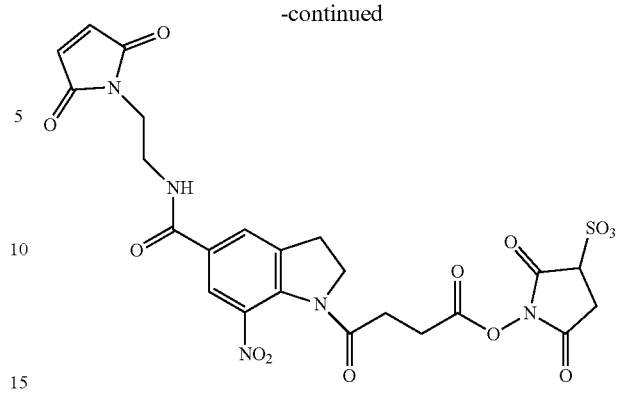

Peptides described above can comprise natural amino acids, non-natural amino acids, or both natural and non-natural amino acids. The term, "amino acid" includes the residues of the natural α-amino acids (Ala, Arg, Asn, Asp, Cys, Glu, Gln, Gly, His, Lys, Ile, Leu, Met, Phe, Pro, Ser, Thr, Trp, Tyr, and Val) in D or L form, as well as β-amino acids, synthetic and non-natural amino acids. Many types of amino acid residues are useful in the polypeptides and the invention is not limited to natural, genetically-encoded amino acids. Non-natural amino acids include, but are not limited to α-aminobutyric acid Abu L-N-methylalanine (Nmala), α-amino-α-methylbutyrate (Mgabu), L-N-methylarginine (Nmarg), aminocyclopropane-carboxylate (Cpro), L-N-methylasparagine (Nmasn), L-N-methylaspartic acid (Nmasp), aminoisobutyric acid (Aib), L-N-methylcysteine (Nmcys), aminonorbomyl-carboxylate cyclohexylalanine (Norb), L-N-methylglutamine (Nmgln), L-N-methylglutamic acid (Nmglu), Chexa L-N-methylhistidine (Nmhis), cyclopentylalanine (Cpen), L-N-methylisolleucine (Nmile), D-alanine Dal L-N-methylleucine (Nmleu), D-arginine (Darg), L-N-methyllysine (Nmlys), D-aspartic acid (Dasp), L-N-methylmethionine (Nmmet), D-cysteine (Dcys), L-N-methylnorleucine (Nmnle), D-glutamine (Dgln), L-N-methylnorvaline (Nmnva), D-glutamic acid (Dglu), L-N-methylornithine (Nmorn), D-histidine (Dhis), L-N-methylphenylalanine (Nmphe), D-isoleucine (Dile), L-N-methylproline (Nmpro), D-leucine (Dleu), L-N-methylserine (Nmser), D-lysine (Dlys), L-N-methylthreonine (Nmthr), D-methionine (Dmet), L-N-methyltryptophan (Nmtrp), D-ornithine (Dorn), L-N-methyltyrosine (Nmtyr), D-phenylalanine (Dphe), L-N-methylvaline (Nmval), D-proline (Dpro), L-N-methylethylglycine (Nmetg), D-serine (Dser), L-N-methyl-t-butylglycine (Nmtbug), D-threonine (Dthr), L-norleucine (Nle), D-tryptophan (Dtrp), L-norvaline (Nva), D-tyrosine (Dtyr), α-methyl-aminoisobutyrate (Maib), D-valine (Dual), α-methyl-γ-aminobutyrate (Mgabu), D-α-methylalanine (Dmala), α-methylcyclohexylalanine (Mchexa), D-α-methylarginine (Dmarg), α-methylcylcopentylalanine (Mcpen), D-α-methylasparagine (Dmasn), α-methyl-α-napthylalanine (Manap), D-α-methylaspartate (Dmasp), α-methylpenicillamine (Mpen), D-α-methylcysteine (Dmcys), N-(4-aminobutyl)glycine (Nglu), D-α-methylglutamine (Dmgln), N-(2-aminoethyl)glycine (Naeg), D-α-methylhistidine (Dmhis), N-(3-aminopropyl)glycine (Norn), D-α-methylisoleucine (Dmile), N-amino-α-methylbutyrate (Nmaabu), D-α-methylleucine (Dmleu), α-napthylalanine (Anap), D-α-methyllysine (Dmlys), N-benzylglycine (Nphe), D-α-methylmethionine (Dmmet), N-(2-carbamylethyl)glycine (Ngln), D-α-methylornithine (Dmorn), N-(carbamylmethyl)glycine (Nasn), D-α-methylphenylalanine (Dmphe), N-(2-carboxyethyl)glycine (Nglu), D-α-methylproline (Dmpro), N-(carboxymethyl)glycine (Nasp), D-α-methylserine (Dmser), N-cyclobutylglycine (Ncbut), D-α-methylthreonine (Dmthr), N-cycloheptylglycine (Nchep), D-α-methyltryptophan (Dmtrp), N-cyclohexylglycine (Nchex), D-α-methyltyrosine (Dmty), N-cyclodecylglycine (Ncdec), D-α-methylvaline (Dmval), N-cylcododecylglycine (Ncdod), D-N-methylalanine (Dnmala), N-cyclooctylglycine (Ncoct), D-N-methylarginine (Dnmarg), N-cyclopropylglycine (Ncpro), D-N-methylasparagine (Dnmasn), N-cycloundecylglycine (Ncund), D-N-methylaspartate (Dnmasp), N-(2,2-diphenylethyl)glycine (Nbhm), D-N-methylcysteine (Dnmcys), N-(3,3-diphenylpropyl)glycine (Nbhe), D-N-methylglutamine (Dnmgln), N-(3-guanidinopropyl)glycine (Narg), D-N-methylglutamate (Dnmglu), N-(1-hydroxyethyl)glycine (Nthr), D-N-methylhistidine (Dnmhis), N-(hydroxyethyl))glycine (Nser), D-N-methylisoleucine (Dnmile), N-(imidazolylethyl))glycine (Nhis), D-N-methylleucine (Dnmleu), N-(3-indolylyethyl)glycine (Nhtrp), D-N-methyllysine (Dnmlys), N-methyl-γ-aminobutyrate (Nmgabu), N-methylcyclohexylalanine (Nmchexa), D-N-methylmethionine (Dnmmet), D-N-methyloniithine (Dnmorn), N-methylcyclopentylalanine (Nmcpen), N-methylglycine (Nala), D-N-methylphenylalanine (Dnmphe), N-methylaminoisobutyrate (Nmaib), D-N-methylproline (Dnmpro), N-(1-methylpropyl)glycine (Nile), D-N-methylserine (Dnmser), N-(2-methylpropyl)glycine (Nleu), D-N-methylthreonine (Dnmthr), D-N-methyltryptophan (Dnmtrp), N-(1-methylethyl)glycine (Neal), D-N-methyltyrosine (Dnmtyr), N-methyla-napthylalanine (Nmanap), D-N-methylvaline (Dnmval), N-methylpenicillamine (Nmpen), γ-aminobutyric acid (Gabu), N-(p-hydroxyphenyl)glycine (Nhtyr), L-t-butylglycine (Tbug), N-(thiomethyl)glycine (Ncys), L-ethylglycine (Etg), penicillamine (Pen), L-homophenylalanine (Hphe), L-α-methylalanine (Mala), L-α-methylarginine (Marg), L-α-methylasparagine (Masn), L-α-methylaspartate (Masp) L-α-methyl-t-butylglycine (Mtbug), L-α-methylcysteine (Mcys) L-methylethylglycine (Metg), L-α-methylglutamine (Mgln), L-α-methylglutamate (Mglu), L-α-methylhistidine (Mhis), L-α-methylhomophenylalanine (Mhphe), L-α-methylisoleucine (Mile), N-(2-methylthioethyl)glycine (Nmet), L-α-methylleucine (Mleu), L-α-methylly sine (Mlys), L-α-methylmethionine (Mmet), L-α-methylnorleucine (Mnle), L-α-methylnorvaline (Mnva), L-α-methylornithine (Morn), L-α-methylphenylalanine (Mphe), L-α-methylproline (Mpro), L-α-methylserine (Mser), L-α-methylthreonine (Mthr), L-α-methyltryptophan (Mtrp), L-α-methyltyrosine (Mtyr), L-α-methylvaline (Meal), L-N-methylhomophenylalanine (Nmhphe), N—(N-(2,2-diphenylethyl)carbamylmethyl)glycine (Nnbhm), N—(N-(3,3-diphenylpropyl) carbamylmethyl)glycine (Nnbhe), or 1-carboxy-1-(2,2-diphenyl-ethylamino)cyclopropane (Nmbc), and the like.

B. Method of Making

The photoreactive amino acid building blocks to be used in the construction of the peptides by Fmoc-strategy-based solid phase peptide synthesis can be prepared by:

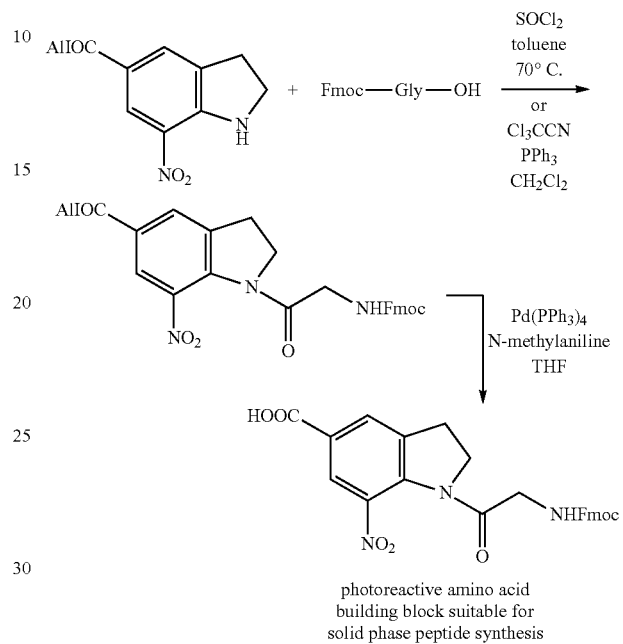

photoreactive amino acid
building block suitable for
solid phase peptide synthesis The peptides are synthesized by standard solid phase peptide synthesis using the Fmoc/t-Bu strategy. For example, resins like Rink Amide resin can be used; the Fmoc groups can be removed with 20% piperidine in N-methylpyrrolidone; coupling can be achieved with 2-(1H-benzotriazol-1-yl)-1,1,3,3-tetramethyluronium hexafluorophosphate (HBTU); N-hydroxybenzotriazole can be used as an auxiliary nucleophile; cleavage from the resin and simultaneous side chain deprotection can be achieved with 95% trifluoroacetic acid in the presence of cation scavengers, e.g. water and triisopropylsilane. Purification can be achieved by precipitation, size exclusion chromatography and/or reversed phase chromatography.

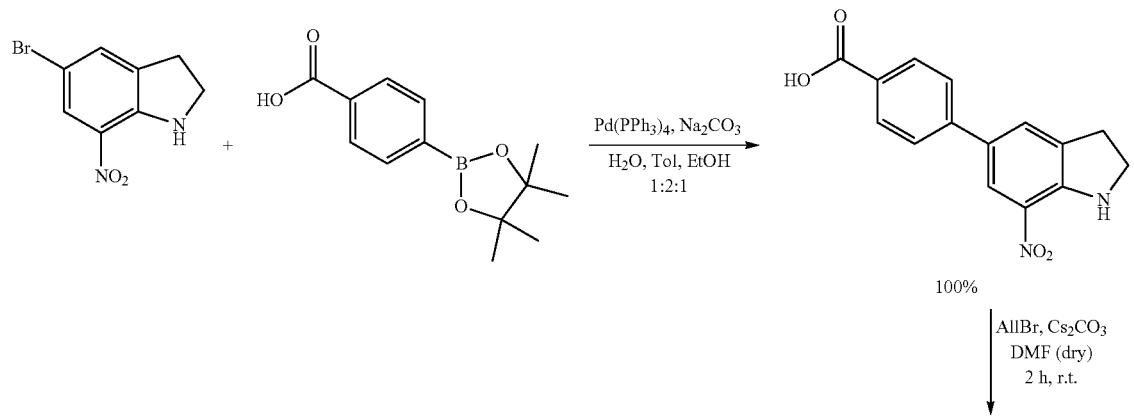

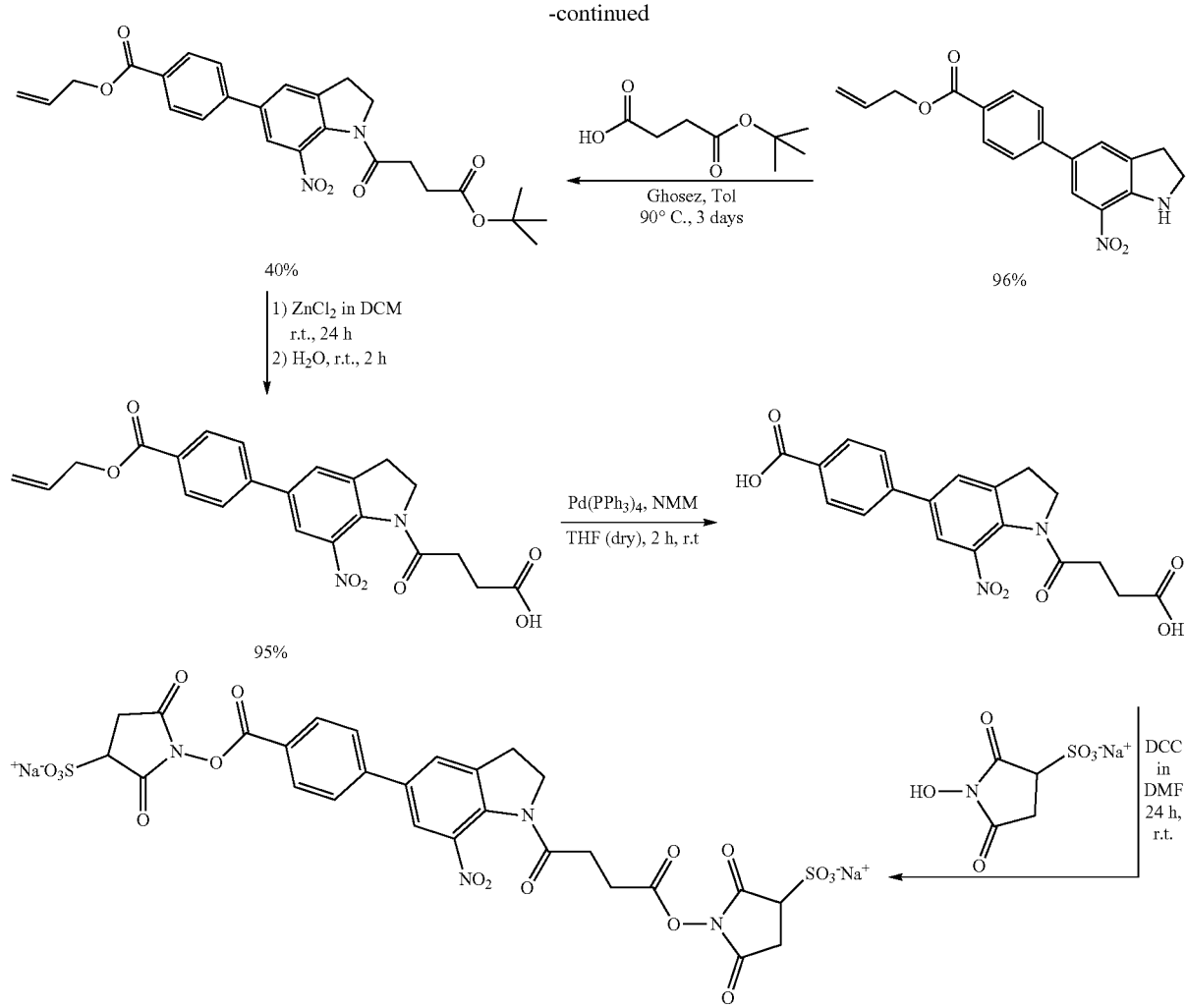

C. Method of Use

The photoreactive peptides can exist in solid forms or hydrogels. Since they contain N-acyl-7-nitroindoline moieties they have an absorption at ~350 nm. Absorption of light of the appropriate wavelength induces photocleavage of chemical bonds at the irradiated spot. This photolysis can be achieved either with near UV light or blue light at 410 nm via one-photon absorption, or with IR light via multi-photon absorption. The demonstrated example in this petition is achieved with a femtosecond laser with a wavelength range of 700 to 750 nm. The irradiated (photo-decomposed) material can be removed from the original form via physical or chemical processes, such as washing or electrochemical separation. This technique allows for photolytically "carving out" patterns, e.g. channels, which might find application in 2D or 3D pattern fabrication. Furthermore, tunnels can be photolytically "carved out" of a macroscopic hydrogel with a femtosecond laser. The latter is a subtractive manufacturing technique leading to a scaffold that can be applied in tissue engineering.

D. Photoreactive Crosslinkers

The photoreactive cross-linkers can be prepared by:

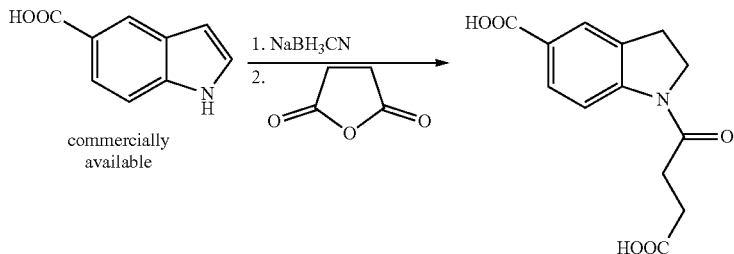

-continued
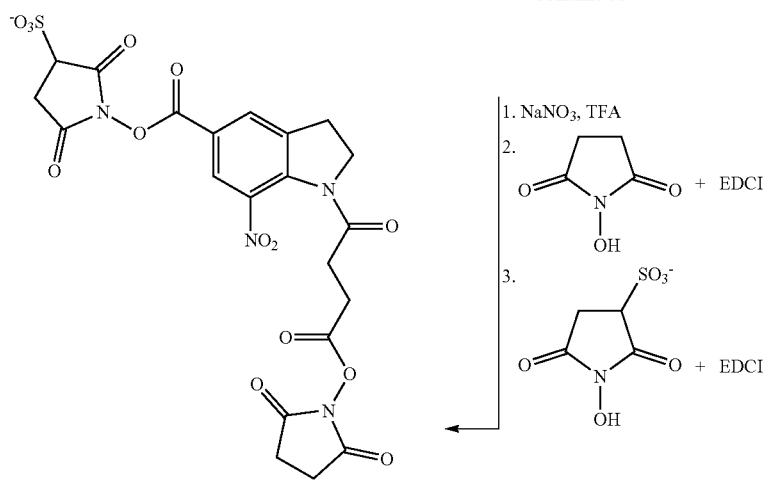
or
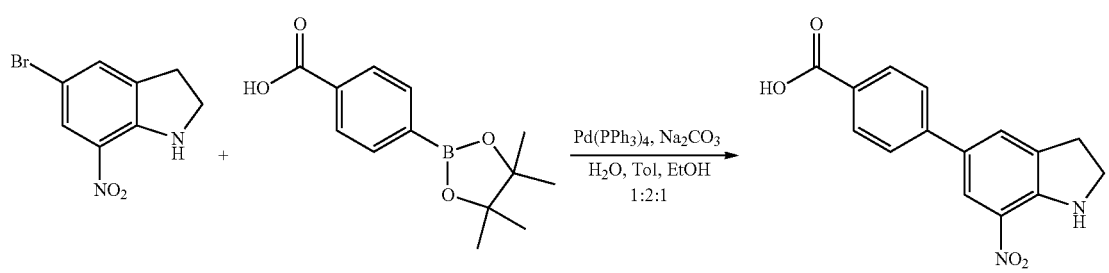
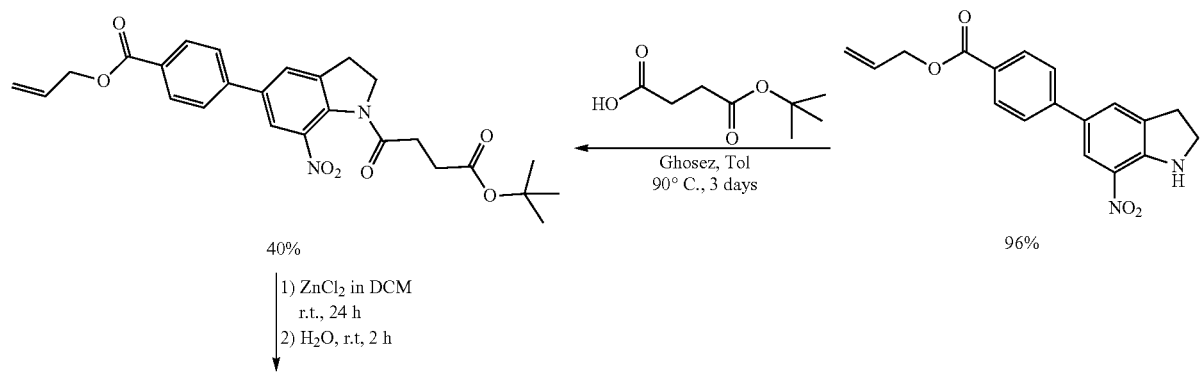
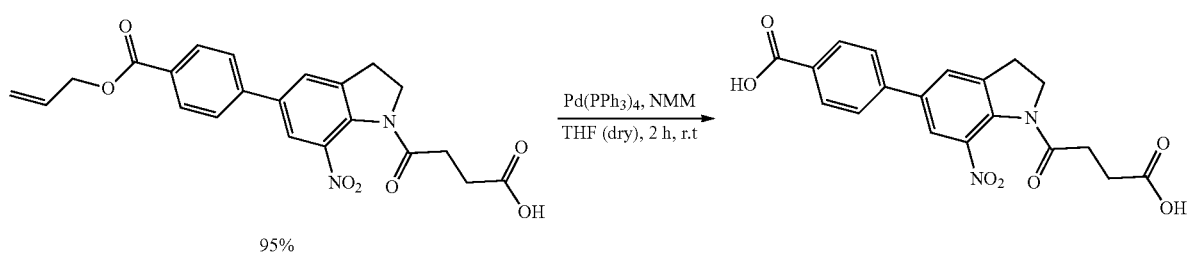

In one or more illustrative examples, the novel crosslinkers consist of an amide or thiocarbamate of 7-nitroindoline, which is the photoreactive core, with at least two reactive groups attached to for crosslinking capability. The photo-cleavability of the invented crosslinkers is based on the known photolysis behavior of N-acyl-7-nitroindolines, and the photolysis behavior of amides and thiocarbamates of 7-nitroindolines. These crosslinkers enable crosslinking of biopolymers, which can be reversed by illumination with light.

Bifunctional Crosslinkers. In one or more illustrative examples, the photoreactive crosslinkers can be, but are not limited to:

bifunctional 7-nitroindoline crosslinkers with amide at position 1 bifunctional 7-nitro-5-phenylinoline crosslinkers with amide at position 1 bifunctional 7-nitroindoline crosslinkers with thiocarbamate at position 1 and bifunctional 7-nitro-5-phenylnitroinoline crosslinkers with thiocarbamate at position 1

Crosslinker Reactive Groups. Reactive groups $R_1$ and $R_2$ are attached to the crosslinkers for crosslinking capability. A variety of reactive groups can be attached.

In one or more illustrative examples, reactive group $R_1$ can be, but is not limited to:

terminal carboxyl groups terminal aldehyde groups terminal epoxides terminal azides terminal N-hydroxysucciminide ester wherein A is H or SO$_3^-$ terminal maleimides

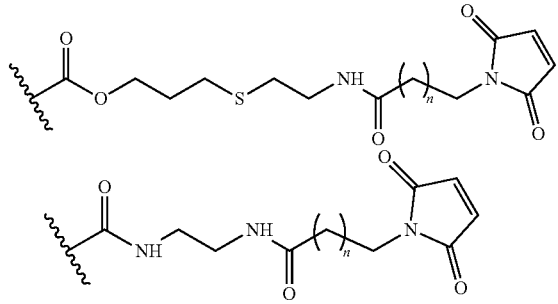

wherein n=1-6
and terminal maleimides with PEG

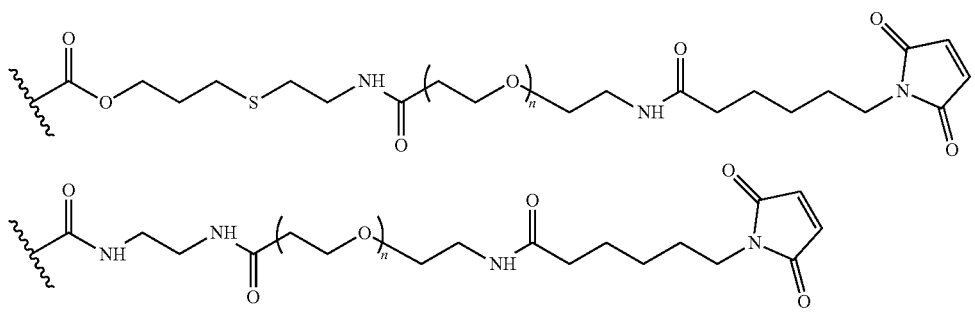

wherein n=1-50

In one or more illustrative examples, reactive group R$_2$ can be, but is not limited to:

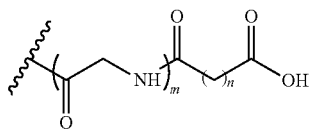

terminal carboxyl groups wherein m = 0-1 and n = 1-6

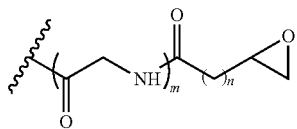

terminal epoxides wherein m = 0-1 and n = 1-10

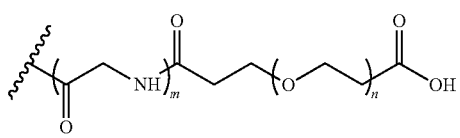

terminal carboxyl group with PEG wherein m = 0-1 and n = 1-50

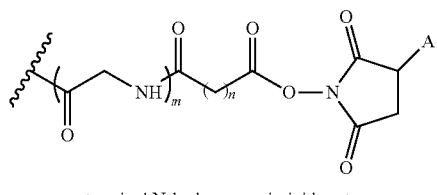

terminal N-hydroxysucciminide ester wherein A is H or SO$_3^-$, m = 0-1, and n = 1-6

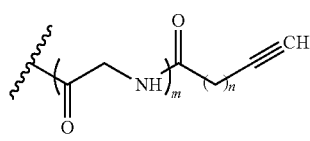

terminal alkyne wherein m = 0-1, and n = 1-5

-continued

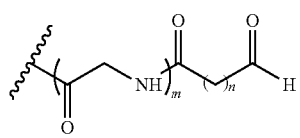

terminal N-hydroxysucciminide ester with PEG wherein A is H or SO$_3^-$, m = 0-1, and n = 1-50

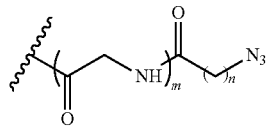

terminal aldehyde wherein m = 0-1, and n = 1-10 terminal azide wherein m = 0-1, and n = 0-6

-continued

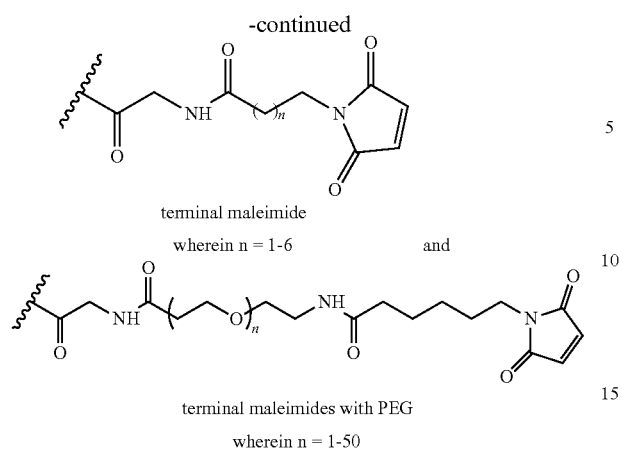

terminal maleimide
wherein n = 1-6 and terminal maleimides with PEG
wherein n = 1-50

Multifunctional Crosslinkers. In one or more illustrative examples, the cross-linker reactive groups can be attached to a multifunctional core, creating a multifunctional cross-linker. For example, reactive groups $R_2$ can be linked to cores such as, but not limited to:

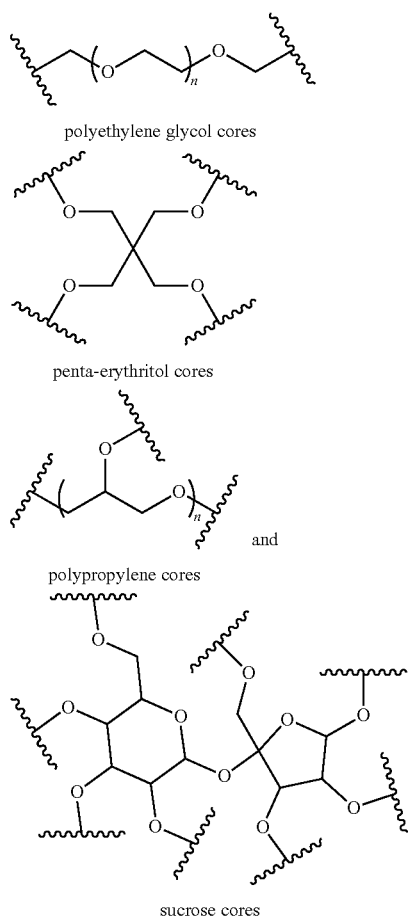

polyethylene glycol cores penta-erythritol cores and polypropylene cores sucrose cores

EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Photolysis of a Peptide with N-Peptidyl-7-Nitroindoline Units Using Two-Photon Absorption Photoremovable protecting groups (PPGs) are required in "caged compounds" in which the function of the original compound is inhibited. Upon photo excitation PPGs are removed and the function of the compound is restored. Such PPGs include arylcarbonylmethyl, nitrobenzyl, nitroindolinyl, and their derivatives, amongst others (Klan et al., *Chemical Reviews* 113(1), 119-91 (2013)). Currently the most common application of this photolysis process is the spatially and temporally controlled release ("uncaging") of bioactive molecules such as neurotransmitters, carboxylic acids, ATP, Ca2+ ions, fragrances, etc. (Ellis-Davies, Nat Meth 4(8), 619-28 (2007); Herrmann, *Photochemical & Photobiological Sciences* 11(3), 446-459 (2012)). Uncaging can also be used for the photochemical conversion of weakly or non-fluorescent molecules into strongly fluorescent ones (Li and Zheng, *Photochemical & Photobiological Sciences* 11(3), 460-71 (2012)). In each of the above applications, the purpose of inducing photolysis is to release compounds with the desired bioactivity or physical property. The inventors explore a new use of photolysis for the potential fabrication of new materials that may serve as scaffolds or matrices for tissue engineering. Within a macroscopic gel-like material bonds may be cleaved only at the light illuminated locations. The molecular fragments generated by photolysis (FIG. 1a) are no longer of interest; and upon their removal from the macroscopic material, three-dimensional structures may be left behind. This approach can potentially achieve similar results as two-photon polymerization-based microfabrication (Farsari and Chichkov, *Nat Photon* 3(8), 450-52 (2009)), albeit by a different mechanism. As one example, a gel-forming peptide with certain strategically placed, photoreactive groups (FIG. 1a) can serve as a source for such a material.

Figure 1B:
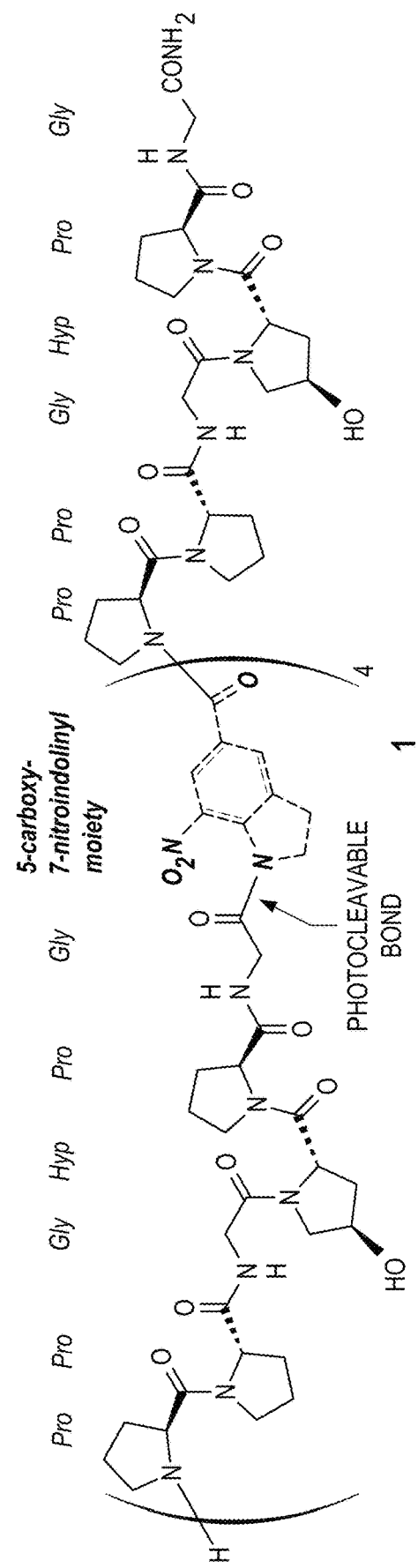

The inventors have synthesized a peptide that resembles collagen in terms of amino acid composition with four photocleavable 7-nitroindoline moieties built into the peptide backbone, peptide 1 (FIG. 1b) (Ornelas et al., unpublished data, (2016)). Collagen mimicking peptides (CMPs) are commonly used materials in tissue engineering to mimic either structural or functional characteristics of natural collagens which aims at engineering higher order structures similar to natural tissue scaffolds (Yu et al., (2011) *Soft Matter* 7, 7927-38). When compared to natural collagen, the benefits of using CMPs include the ability for customization as well as reversible melting behavior with complete efficiency once the CMP is cooled due to its small size (Yu et al., (2011) *Soft Matter* 7, 7927-38).

N-acyl-nitroindoline based PPGs typically have broad absorption spectra in the wavelength range shorter than 500 nm (Papageorgiou et al., (2005) *Photochem. Photobiol. Sci.* 4, 887-96; Papageorgiou et al., (1999) *J. Am. Chem. Soc.*

121, 6503-04). Based on the success of two-photon uncaging of a methoxy derivative of nitroindolino glutamate (Matsuzaki et al., *Nat Neurosci* 4(11), 1086-92 (2001)), the inventors explored the feasibility of using an in-house developed two-photon microscope to cleave the amide bonds of the N-peptidyl-7-nitroindoline units within the newly synthesized peptide 1 (Acosta et al., (2014) *Biomed. Opt. Express* 5, 3990-4001). Two-photon absorption has the advantage of confined spatial excitation at the focal volume due to its nonlinearity characteristic. It is also convenient to incorporate two-photon absorption-based photolysis into commonly used two-photon fluorescence microscopes to achieve high spatiotemporal resolution for microfabrication. In addition, the fluorescence decay of N-acyl-7-nitroindolines can be measured with these imaging microscopes.

A. Methods

Synthesis. Briefly, the photoreactive peptide 1 was assembled by on-resin fragment condensation using Fmoc/t-Bu strategy solid phase peptide synthesis (SPPS). The C-terminal hexapeptide was synthesized on Rink amide resin and elongated four times with the photoreactive hexapeptide, which had been synthesized by SPPS using diphenyl diazomethane resin and a photoreactive glycine building block (Hogenauer et al., (2007) *Org. Biomol. Chem.* 5, 759-62; Pardo et al., (2015) *Chem Bio Chem* 16, 1884-89) under standard coupling and deprotection conditions (FIG. 2). The crude polypeptide was purified by reversed phase Fast Protein Liquid Chromatography and lyophilized.

Two-photon microscope. The details of the in-housed developed two-photon microscope was previously described (Acosta et al., (2014) Biomed. Opt. Express 5, 3990-4001). In summary the light source is a mode-locked Ti:Sapphire laser (Maitai H P, 690-1040 nm, 100 fs, 80 MHz, Newport, Santa Clara, Calif.). The inventors have used 710 nm light to achieve two-photon excitation of N-acyl-nitroindoline. The home-built x-y scanner (polygon, galvanometer) can achieve 30 frames/s scanning rate. The laser power at the sample site is varied by rotating a half-wave plate in front of a polarizer. The fluorescence signal from the sample are detected in three spectral channels with photomultiplier tubes (PMTs): red (570-616 nm), green (500-550 nm), and blue (417-477 nm). The outputs of these three PMTs are fed into red/green/blue channels of a frame grabber (Solios eA/XA, Matrox, Quebec, Canada). Two-dimensional images in the x-y plane are acquired through a home-built software program. Each frame has 500×500 pixels. Each final static image is an average of 30 frames.

B. Results

The lyophilized peptide 1 (~1 mg) was dissolved in 2 µL of water on a microscope slide to give a yellow (~125 mM) solution. At this concentration, peptide 1 quickly forms a gel. The film/gel was covered with a cover slip (FIG. 3a).

Figures 4A, 4B, 4C, 4D:
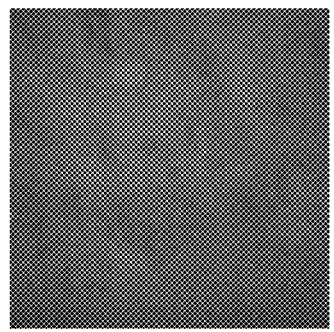
FIGS. 4A-F. Fluorescence images and quantified decay of peptide 1. (A) Fluorescence image taken at 1 minute with laser power of 200 mW; (B) 2 minutes image; (C) 4 minutes image; (D) 8 minutes image; (E) Normalized fluorescence decay data and fitting curves for varied laser power; (F) Double-log plot of reaction rate vs. laser intensity for the synthetic photoreactive peptide 1.
Figure 4F:
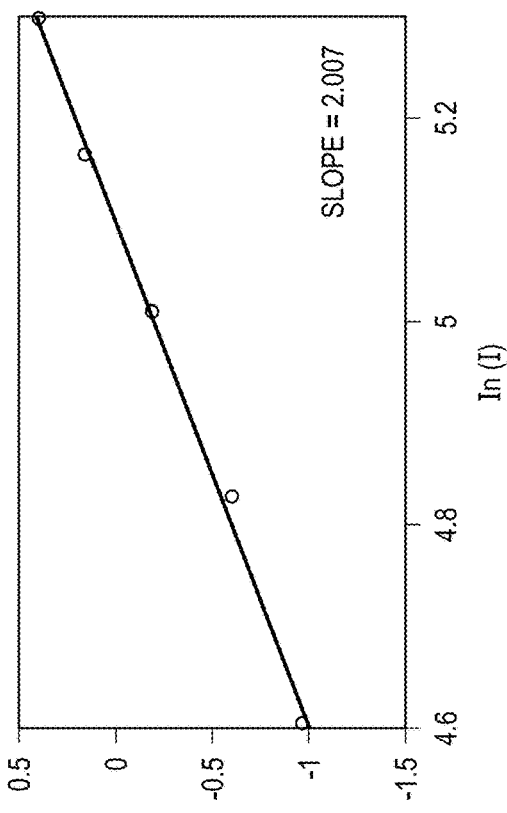
Figure 4E:
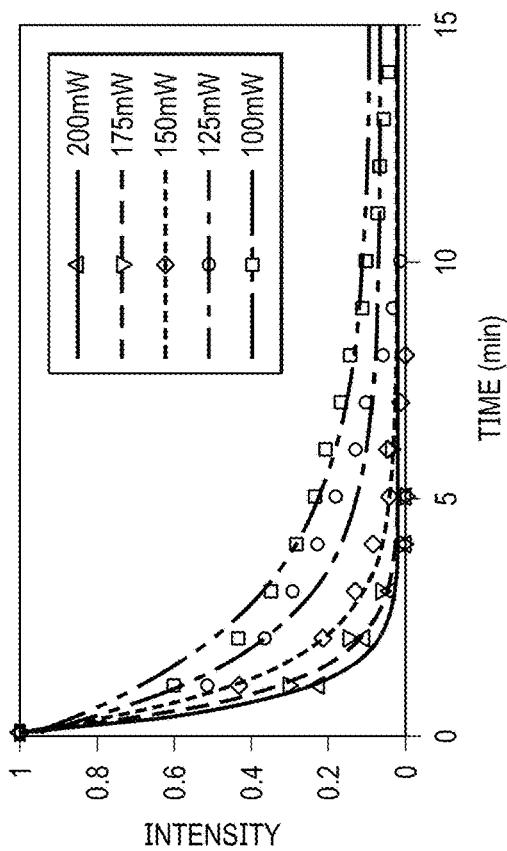

Several spots within the sample were irradiated under the two-photon microscope using 710 nm light with varying excitation laser output powers ranging from 100 to 200 mW with increments of 25 mW. The delivered laser power at the sample location is 10% of such values. Upon excitation, the photoreactive peptide 1 emits fluorescent light which is collected using both red and green PMTs. This excitation also induces photolysis of the amide bond between glycine and 7-nitroindoline, producing non-fluorescent nitroindoline and/or 7-nitrosoindole derivatives (spots in FIG. 3b), which are darker in color than the N-acylated nitroindoline precursor 1. Therefore, as the photolysis reaction progresses, the fluorescent peptide 1 is consumed, and consequentially a decrease in average fluorescence intensity at the irradiation site is observed. For each irradiated spot, a time series of fluorescence images was recorded at every minute to track the fluorescence intensity decay throughout the photo induced reaction process (FIG. 4a-4d). Once the fluorescence decay appeared to reach a plateau, the laser irradiation at this spot was stopped and a new location was chosen to repeat the process with a different laser power. To quantify fluorescence decay, a defined region of interest was chosen within the image, and the average fluorescence intensity in each of the green and red channels was measured. This measurement was repeated for the same region of interest for every image in each time series. These fluorescence decay curves from a single sample of peptide 1 are shown in FIG. 4e.

These fluorescence decay data were fitted using an exponential decay regression line of the form $F(t)=F_0 e^{-\beta t}$, where $\beta$, is the fluorescence decay rate. This was done using the curve fitting module in MATLAB. As mentioned before, the decrease in fluorescence intensity correlates with the photolytic reaction of the compound under the incident light. Therefore, the fluorescence decay rate $\beta$ is also the photolysis reaction rate within the focus of the sample. Since the photolysis is occurring as a result of two-photon absorption, the photolysis reaction rate is proportional to the probability of two-photon absorption as shown in Eq. (1) where I is the excitation laser power.

$$\beta \alpha I^2 \qquad \text{(Eq. 1)}$$

Plotting log (I) versus log ($\beta$) for each of the laser intensities and their corresponding fluorescence decay rates produces a linear graph whose slope should be 2 for a two-photon process. Therefore, the photochemical reaction rate's quadratic dependence on laser intensity may easily be evaluated using a double-log plot. The slope of the regression line in the double-log plot in FIG. 4f is 2.007, which clearly exhibits the two-photon absorption induced nature of the photolysis within the synthetic 34-mer peptide 1.

Figure 5:
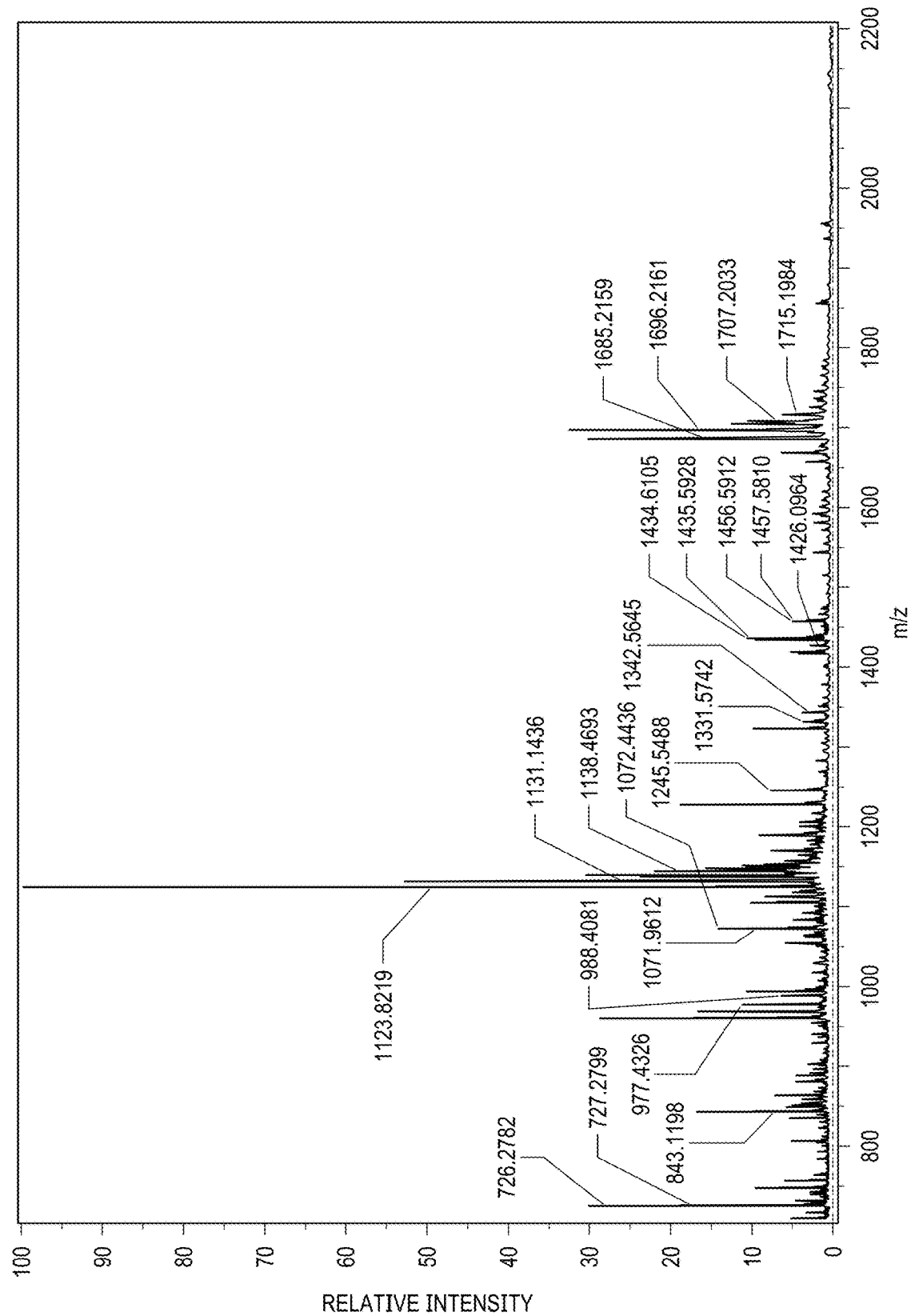
FIG. 5. High Resolution Electrospray Ionization-Time of Flight mass spectrum of the crude mixture obtained after irradiation of peptide 1 (sample in FIG. 3b). Reported are the monoisotopic masses for each peptide 1 (C156H197N39O47): m/Z for [M+4H]4+ calc. 843.1134, found 843.1198; m/Z for [M+3H]3+ calc. 1123.8153, found 1123.8219; m/Z for [M+2H+Na]3+ calc. 1131.1426, found 1131.1436; m/Z for [M+H+2Na]3+ calc. 1138.4699, found 1138.4693; m/Z for [M+2H]2+ calc. 1685.2190, found 1685.2159; m/Z for [M+H+Na]2+ calc. 1696.2100, found 1696.2161. 2 (C33H42N8O11): m/Z for [M+H]+ calc. 727.3051, found 727.2799. 3 (C33H43N9O10): m/Z for [M+H]+ calc. 726.3211, found 726.2782. 4 (C66H82N16O21): m/Z for [M+H]+ calc. 1435.5919, found 1435.5928; m/Z for [M+Na]+ calc. 1457.5738, found 1457.5810. 5 (C66H83N17O20): m/Z for [M+H]+ calc. 1434.6079, found 1434.6105; m/Z for [M+Na]+ calc. 1456.5898, found 1456.5912. 6 (C57H76N14O18): m/Z for [M+H]+ calc. 1245.5540, found 1245.5488. 7 (C99H122N24O31): m/Z for [M+2H]2+ calc. 1072.4432, found 1072.4436. 8 (C99H123N25O30): m/Z for [M+2H]2+ calc. 1071.9512, found 1071.9612. 9 (C90H116N22O28): m/Z for [M+2H]2+ calc. 977.4243, found 977.4326. 10 (C132H163N33O40): m/Z for [M+2H]2+ calc. 1426.0946, found 1426.0964. 11 (C123H156N30O38): m/Z for [M+2H] 2+ calc. 1331.5677, found 1331.5742.
Figure 6:
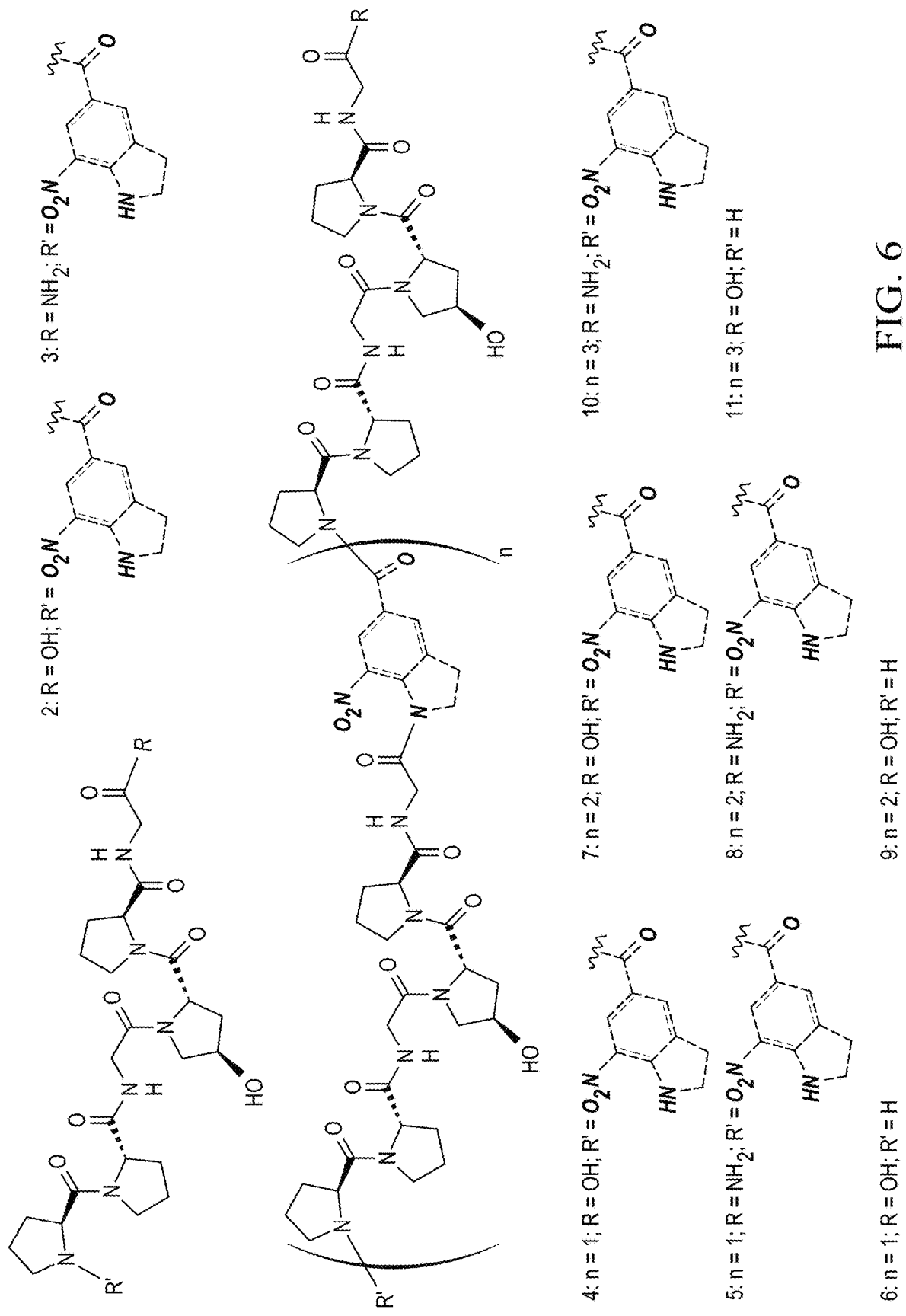
FIG. 6. Photolysis products identified by mass spectrometry.

Analysis of the mass spectrum (FIG. 5) of the crude sample post-irradiation (FIG. 3b) revealed the presence of all eleven expected linear nitroindoline-containing peptide fragments of various lengths (2-11, FIG. 6). Since each molecule contains four photocleavable sites, some molecules may undergo fewer than four photolytic reactions during the short irradiation period. Therefore, it is not surprising to have identified many incompletely photolyzed peptides (5-11) in the crude mixture. Since only a small fraction of the peptide sample was irradiated, the full-length peptide 1 is the major component found in the mass spectrum (FIG. 5). Although the mass spectrum of the crude mixture also contains several unidentified signals, there is no evidence of any cross-linking between peptides.

A further indication for the occurrence of photolysis within irradiation sites is the color change of the sample. The original peptide 1 is bright yellow in color and its color remains the same after being dissolved in water at high concentration. In contrast, the peptide fragments have a dark brown color due to nitroindoline derivatives that are no longer acylated. The color is noticeably different from the original peptide 1 upon visual inspection by comparing FIG. 3a vs. 3b. The positions of dark brown spots formed within the sample match the pre-recorded irradiation locations (FIG. 3b) which, together with the double-log plot of reaction rate vs. laser intensity (FIG. 4f), indicates the two-photon absorption induced photochemical cleavage.

The inventors have studied the ability of a new collagen resembling peptide 1, composed of five Pro-Pro-Gly-Hyp-Pro-Gly (SEQ ID NO:_) hexamers covalently linked together by four 7-nitroindoline groups to undergo two-photon photolysis. Peptide 1 contains four N-peptidyl-7-nitroindoline moieties that are fluorescent and photoreactive. Femtosecond laser induced fluorescence decay experiments show that these N-peptidyl-7-nitroindoline moieties can be cleaved photolytically. The double-log plot of reaction rate vs. laser intensity has a slope of 2, which proves that the photolysis occurred through a two-photon absorption process. This new type of photoreactive material lays the foundation for future research on fabricating three-dimensional microstructures.

Example 2

Figure 7:
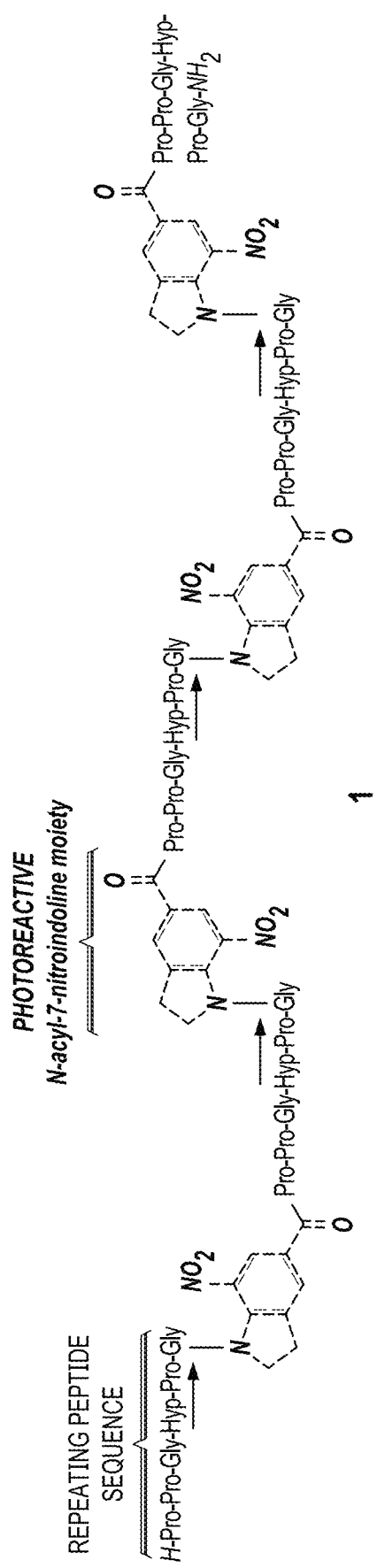
FIG. 7. Photoreactive target peptide 1 with collagen-like repeating units and nitroindoline moieties (red) built into the peptide backbone. Photolytic cleavage occurs at the N-peptidyl-nitroindoline bonds indicated with arrows.

Synthesis of a Collagen-Like Peptide with Photoreactive N-Acyl-7-Nitroindoline Moieties Incorporated into its Backbone The inventors provide an example for the synthesis of a photoreactive 34 amino acid long collagen-like peptide 1 consisting of five hexapeptide repeats that are separated by the unnatural amino acid 5-carboxylic acid-7-nitroindoline (FIG. 7). The inventors also present studies on its secondary structure, its fluorescent and photolytic properties under UV light, and on its ability to support stem cell growth.

In designing a peptide as an underlying compound for the preparation of a network-forming hydrogel whose structure can potentially be modified by photolysis, the following factors can be considered: (a) the amino acid components and length of the peptide; (b) the photochemistry; and (c) the synthetic strategy to access such a material. Collagens are major components in many extracellular matrices, and they play central roles in all phases of wound healing, including cell proliferation, remodeling, hemostasis, and inflammation (Agren, M. S., (Ed.) (2016) *Functional Biomaterials*, Vol. 2, Elsevier Ltd., Amsterdam). To mimic the properties of collagen and other collagen-mimicking peptides, which are typically about 30 amino acids long, (Yu et al., (2011) *Soft Matter* 7, 7927-38; Li and Yu, (2013) *Curr. Opin. Chem. Biol.* 17, 968-75; Hernandez-Gordillo and Chmielewski, (2014) *Biomaterials* 35, 7363-73; Xiao, (2017) *Biophysical Characterization of Collagen Mimic Peptides*, 1 ed., Springer, Singapore.) the inventors chose five hexapeptide repeats rich in glycine, proline, and hydroxyproline, with a glycine residue at every third position within the hexapeptide repeat. Since the ability to undergo photolytic cleavage into small peptide fragments was a required property, the design of the target peptide included four 7-nitroindoline moieties, which can be introduced via the building block N-(Fmoc-Gly)-5-carboxylic acid-7-nitroindoline (Hogenauer et al., (2007) *Org. Biomol. Chem.* 5, 759-62; Pardo et al., (2015) *Chem Bio Chem* 16, 1884-89) in solid phase peptide synthesis (SPPS) using the Fmoc/tBu strategy (Chan and White, (Eds.) (2000) *Fmoc solid phase peptide synthesis: a practical approach*, Vol. 222, Oxford University Press, Oxford). The inventors have shown that this building block is suitable for the installation of a photoreactive moiety at the C-terminus of peptides by SPPS, which can be photochemically converted into aliphatic or aromatic peptide thioesters and peptide hydrazides (Hogenauer et al., (2007) *Org. Biomol. Chem.* 5, 759-62; Pardo et al., (2015) *Chem Bio Chem* 16, 1884-89). The photochemical properties of N-acyl-7-nitroindoline in an inert organic solvent in the presence of water, alcohols, or ammonia were first discovered more than 40 years ago and resulted in the acylation of these nucleophiles, producing carboxylic acids, esters, and amides (Amit et al., (1976) *J. Am. Chem. Soc.* 98, 843-44). Mechanistic studies of the underlying photochemistry suggest that upon light activation of the N-acyl-7-nitroindoline 2, a nitronic anhydride intermediate 3 is formed (Morrison et al., (2002) *Photochem. Photobiol. Sci.* 1, 960-69; Cohen et al., (2005) *Org. Lett.* 7, 2845-48), possibly by a sigmatropic rearrangement (Mendez et al., (2012) *Trends Photochem. Photobiol.* 14, 75-91). In an inert organic solvent, the nitronic anhydride 3 can either acylate a nucleophile (e.g., water) and produce a carboxylic acid and 7-nitroindoline 4 (Scheme 1, path A) (Morrison et al., (2002) *Photochem. Photobiol. Sci.* 1, 960-69; Papageorgiou et al., (2005) *Photochem. Photobiol. Sci.* 4, 887-96), or form a carboxylic acid and nitrosoindole 5 in a photoredox reaction (path B, 100% water). The latter has been exploited for the photorelease of caged amino acids (Papageorgiou et al., (1999) *J. Am. Chem. Soc.* 121, 6503-04). Which of the two paths predominates is solvent-dependent (Morrison et al., (2002) *Photochem. Photobiol. Sci.* 1, 960-69), and is also influenced by the presence or absence of acid. For example, under acidic conditions, path B seems to be preferred, presumably due to protonation of the acyl oxygen of the nitronic anhydrate intermediate 3 (Mendez et al., (2012) *Trends Photochem. Photobiol.* 14, 75-91). Other N-acyl-7-nitroindoline derivatives, with a bromo (Amit et al., (1976) *J. Am. Chem. Soc.* 98, 843-44; Pass et al., (1981) *J. Am. Chem. Soc.* 103, 7674-75; Vizvardi et al., (2003) *Chem. Lett.* 32, 348-49; Simo et al., (2005) *Carbohydr. Res.* 340, 557-66; Kaneshiro and Michael, (2006) *Angew. Chem. Int. Ed.* 45, 1077-81; Hassner et al., (2007) *Synlett*, 2405-2509), nitro (Helgen and Bochet, (2003) *J. Org. Chem.* 68, 2483-86; Débieux et al., (2007) *Eur. J. Org. Chem.*, 2073-77), or a carboxamido substituent (Hogenauer et al., (2007) *Org. Biomol. Chem.* 5, 759-62; Pardo et al., (2015) *Chem Bio Chem* 16, 1884-89; Nicolaou et al., (2001) *Synlett SI*, 900-03) at position 5 of the indoline ring, also undergo photoacylation (path A) with a number of different nucleophiles, including water, in inert organic solvents such as dichloromethane, acetonitrile, tetrahydrofuran, N,N-dimethylformamide, N,N,N',N'-tetramethylurea, dimethylsulfoxide, and N-methylpyrrolidone. With respect to photoreactive peptide 1, photolysis into small heptapeptide fragments with C-terminal glycine residues may occur by either pathway depending on the reaction conditions. The inventors have recently shown that the photolysis of peptide 1 can also be accomplished by a two-photon absorption process (Hatch et al., (2016) *Biomed. Opt. Express* 7, 4654-59). In that experiment, a highly concentrated thin film of peptide 1 in water was irradiated with femtosecond laser light at 710 nm. The mass-spectrometric analysis of the photolysis products showed that all expected peptide fragments formed, and that the photolysis had occurred via path A (Scheme 1) producing peptide fragments with N-terminal 7-nitroindoline moieties (Hatch et al., (2016) *Biomed. Opt. Express* 7, 4654-59). Due to the repeating amino acid sequences in target peptide 1, it lends itself to being synthesized by solid phase peptide synthesis (SPPS) using on-resin peptide fragment condensation.

Scheme 1.
Light activation of an N-acyl-7-nitroindoline, and its solvent-dependent decomposition.
A low water content favors path A, while a higher-water content favors path B
(Morrison et al., (2002) *Photochem. Photbiol. Sci.* 1, 960-69).

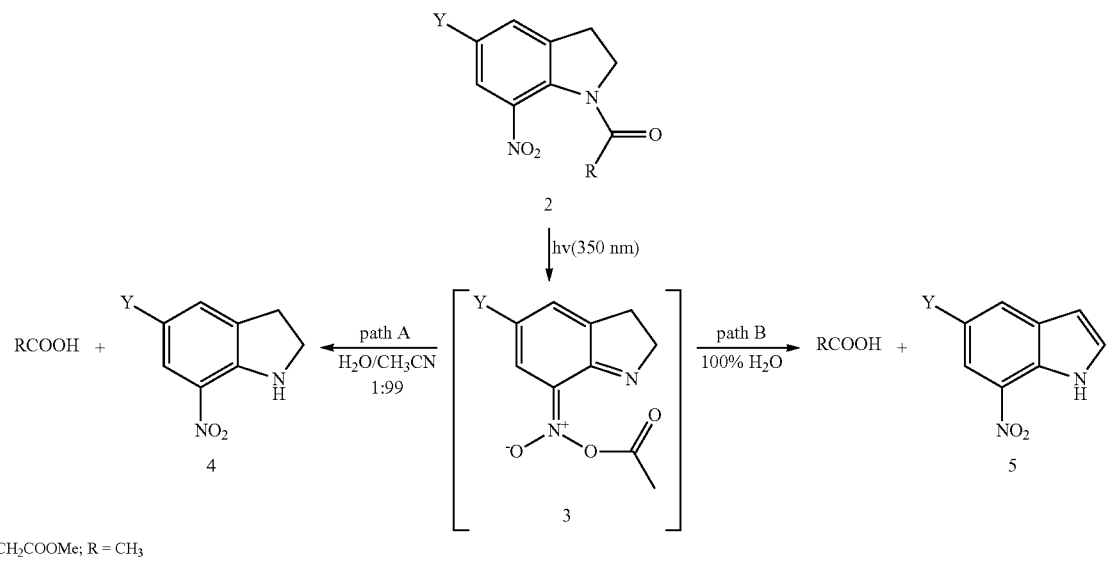

Y = CH$_2$COOMe; R = CH$_3$

A. Results

An example of a target peptide 1 consists of five repeating hexapeptide sequences separated by four photoreactive moieties. The photoreactive glycine building block 6 can be synthesized in seven steps from commercially available starting materials (Hogenauer et al., (2007) *Org. Biomol. Chem.* 5, 759-62; Pardo et al., (2015) *Chem Bio Chem* 16, 1884-89). It was a key component in the synthesis of the protected photoreactive peptide segment 7 (Scheme 2), which was pre-prepared on diphenyldiazomethane resin (Chapman and Walker, (1975) *J. Chem. Soc. Chem. Commun.*, 690-91) for the fragment condensation. Since the attachment of the first amino acid to diphenyldiazomethane resin does not rely on activation with a coupling reagent, this resin is highly suitable for the recovery of unreacted amino acid excess, particularly when it is a precious building block such as the photoreactive glycine derivative 6. The coupling of the remaining Fmoc-protected amino acids and the removal of Fmoc groups was accomplished under standard conditions (Chan and White, (Eds.) (2000) *Fmoc solid phase peptide synthesis: a practical approach*, Vol. 222, Oxford University Press, Oxford). The protected peptide acid 7 was cleaved from the resin with a dilute solution of trifluoroacetic acid in DCM. Scheme 3 shows the assembly of the photoreactive target peptide 1. First, peptide 8 was synthesized by SPPS on Rink Amide resin followed by four on-resin fragment condensations using the pre-prepared photoreactive peptide 7. Global deprotection and cleavage from the resin was accomplished with 95% trifluoroacetic acid (TFA), and purification of the peptide by reversed phase chromatography. Through a combination of semi-automatic Fmoc-SPPS and peptide fragment condensation, a 41% overall yield of 1 was obtained. The peptide was characterized by mass spectrometry, UV-VIS spectrophotometry, and fluorescence spectroscopy, and circular dichroism. The peptide's ability to undergo photolytic cleavage with UV light in an aqueous solution was also investigated. In order to obtain preliminary cell toxicity information, the peptide's ability to support the lateral growth of mesenchymal stem cells was studied.

Figure 8A:
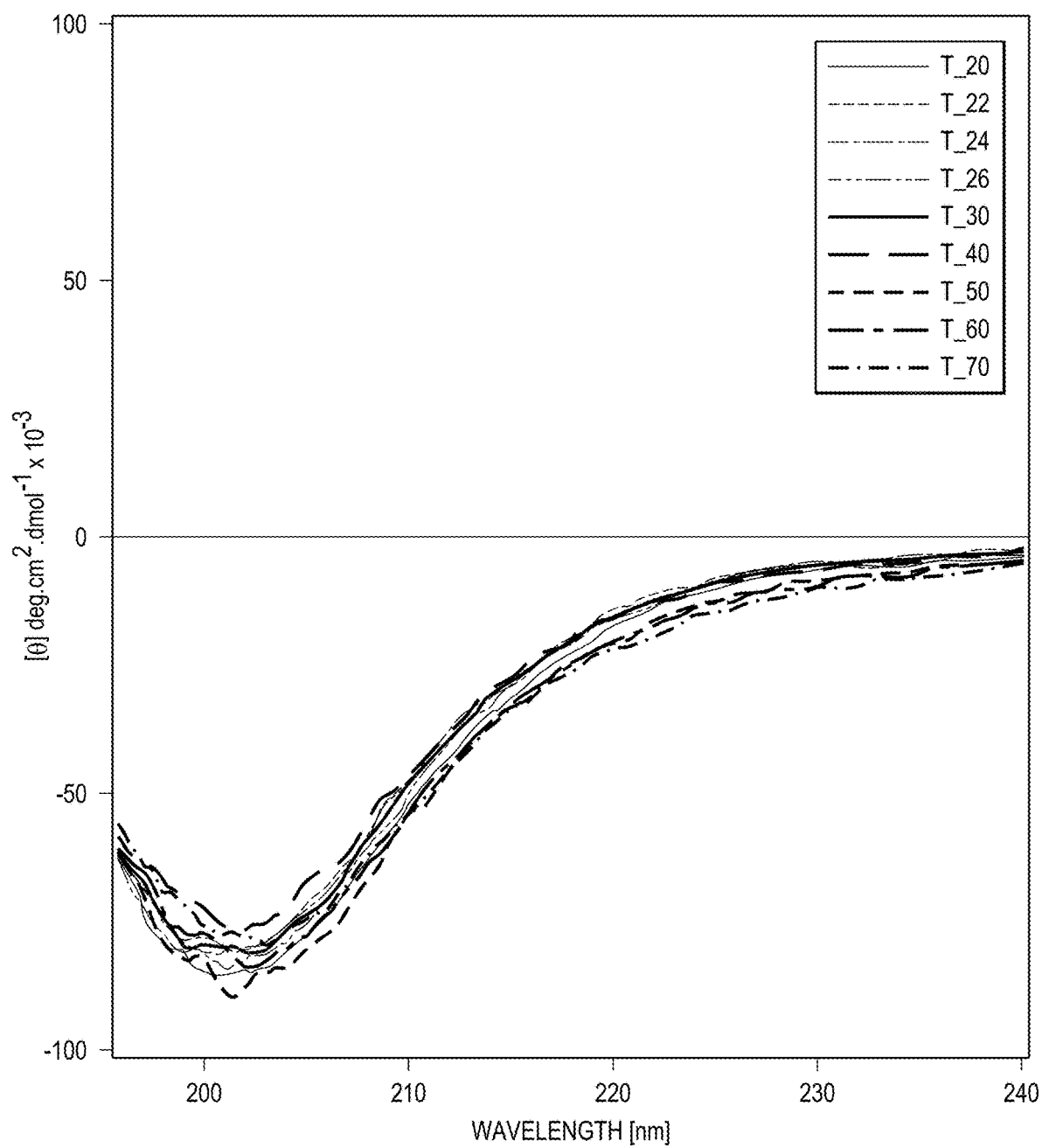
FIGS. 8A-C. Secondary structure determination of the triple helical peptide using far-UV CD. (A) The change in color from blue to red denotes the rise in temperature from 20° C.-70° C.; (B) Mean molar ellipticity at 200 nm at each temperature from 20° C.-70° C.; (D) Mean molar ellipticity at 222 nm at each temperature from 20° C.-70° C.
Figure 8C:
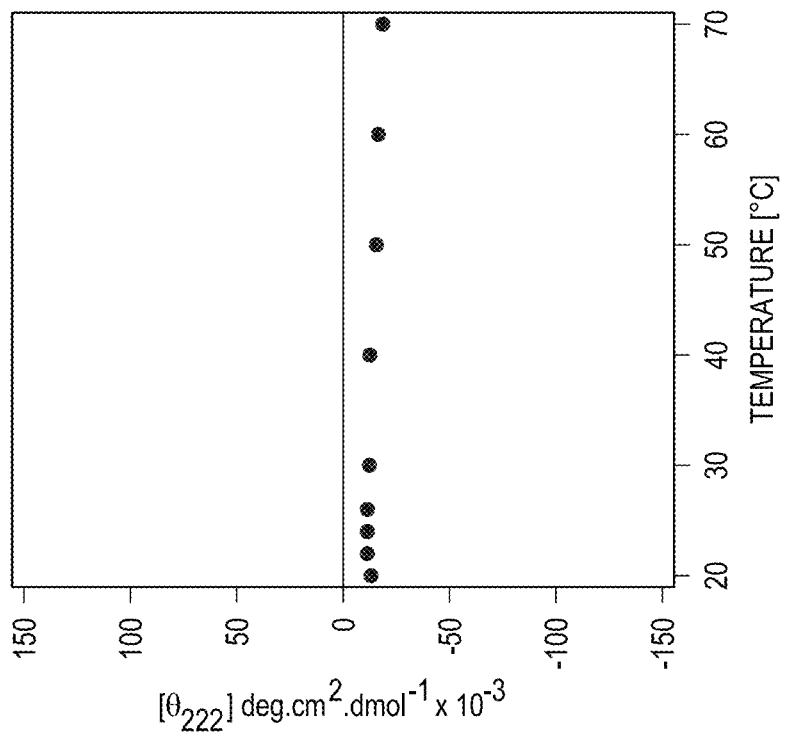
Figure 8B:
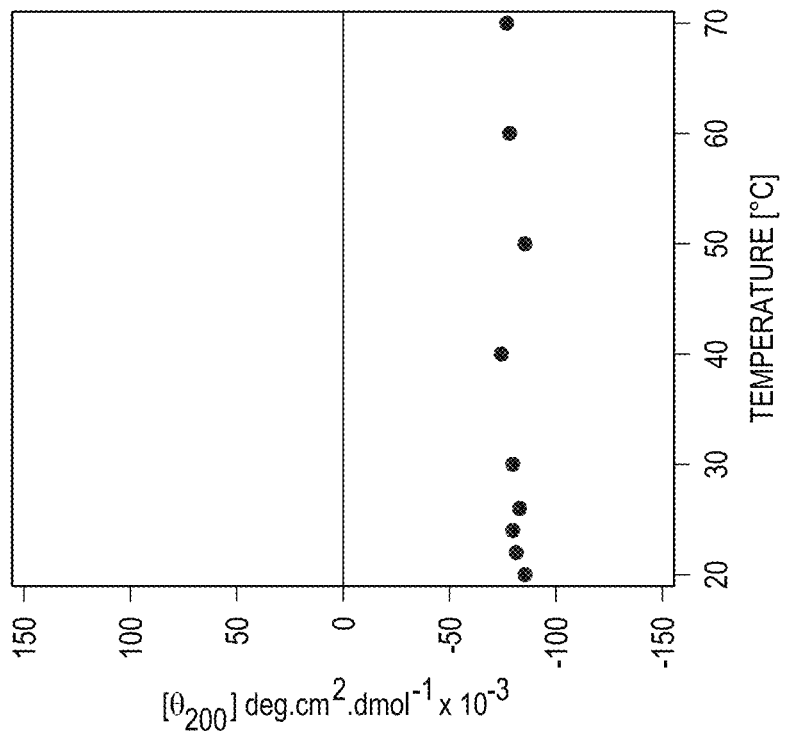
Figure 9:
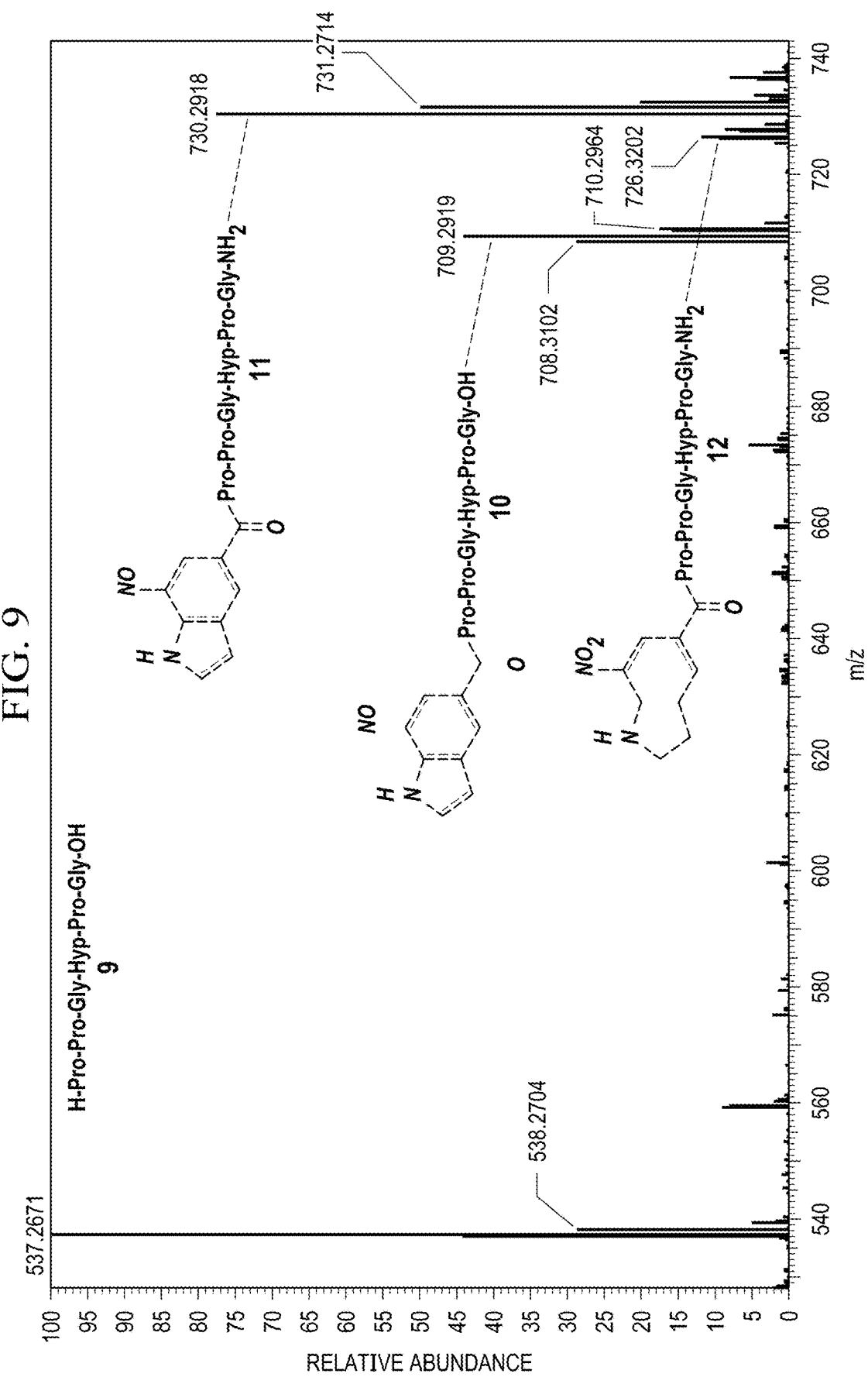
FIG. 9. HR ESI MS after irradiation of peptide 1 with 350 nm light in water. Peptide 9: m/z [M+H]+ calcd. 537.2672, obs. 537.2671; 10: m/z [M+H]+ calcd. 709.2946, obs. 709.2919; peptide 11: m/z [M+Na]+ calcd. 730.2925, obs. 730.2918; 12: m/z [M+H]+ calcd. 726.3211, obs. 726.3202.

The far-UV CD spectra of peptide 1 show the typical signature of a triple helix (FIG. 8a). The overall structure closely resembles the triple helices observed for collagen peptides that consist of naturally occurring amino acids (Persikov et al., (2004) *Protein Sci.* 13, 893-902; Koide, (2007) *Philos. Trans. R. Soc. Lond. B Biol. Sci.* 362, 1281-91; Frank et al., (2001) *J. Mol. Biol.* 308, 1081-89). Increasing the temperature from 20° C. to 70° C. in 10° C. steps shows practically no loss of structure (FIG. 8a). FIGS. 8b and 8c show the mean molar ellipticity at [θ]200 and [θ]222, respectively, with the rise in temperature. There is minimal change in intensity both at 200 nm and 222 nm indicating that the secondary structure of the peptide is stable in the temperature range studied. Unlike other triple helical peptides of similar length (Persikov et al., (2004) *Protein Sci.* 13, 893-902; Leikina et al., (2002) *Proc. Natl. Acad. Sci. U.S.A.* 99, 1314-18; Kotch and Raines, (2006) *Proc. Natl. Acad. Sci. USA* 103, 3028-33), peptide 1 contains four units of the unnatural amino acid 5-carboxylic acid-7-nitroindoline, which could be responsible for its unusual stability. Unlike proteins that consist predominantly of α-helices or β-sheets, the CD spectra of collagen and gelatin have a strong minimum at approximately 200 nm which can be attributed to random coil structures and a positive peak at 222 nm, which is often not a pronounced maximum. Both are typical features of the CD spectra of collagen (Gopal et al., (2012) *Int. J. Mol. Sci.* 13, 3229-44). Importantly, the structure formed by peptide 1 is very stable at physiological temperature, i.e., at 37° C., which is highly significant as it enhances its utility for biological applications. Peptide 1 that has a stable collagen-like structure could be useful for cell adherence and growth.

Scheme 2.
SPPS of the protected photoreactive peptide 7 on diphenyldiazomethane resin using a photoreactive glycine building block (6).
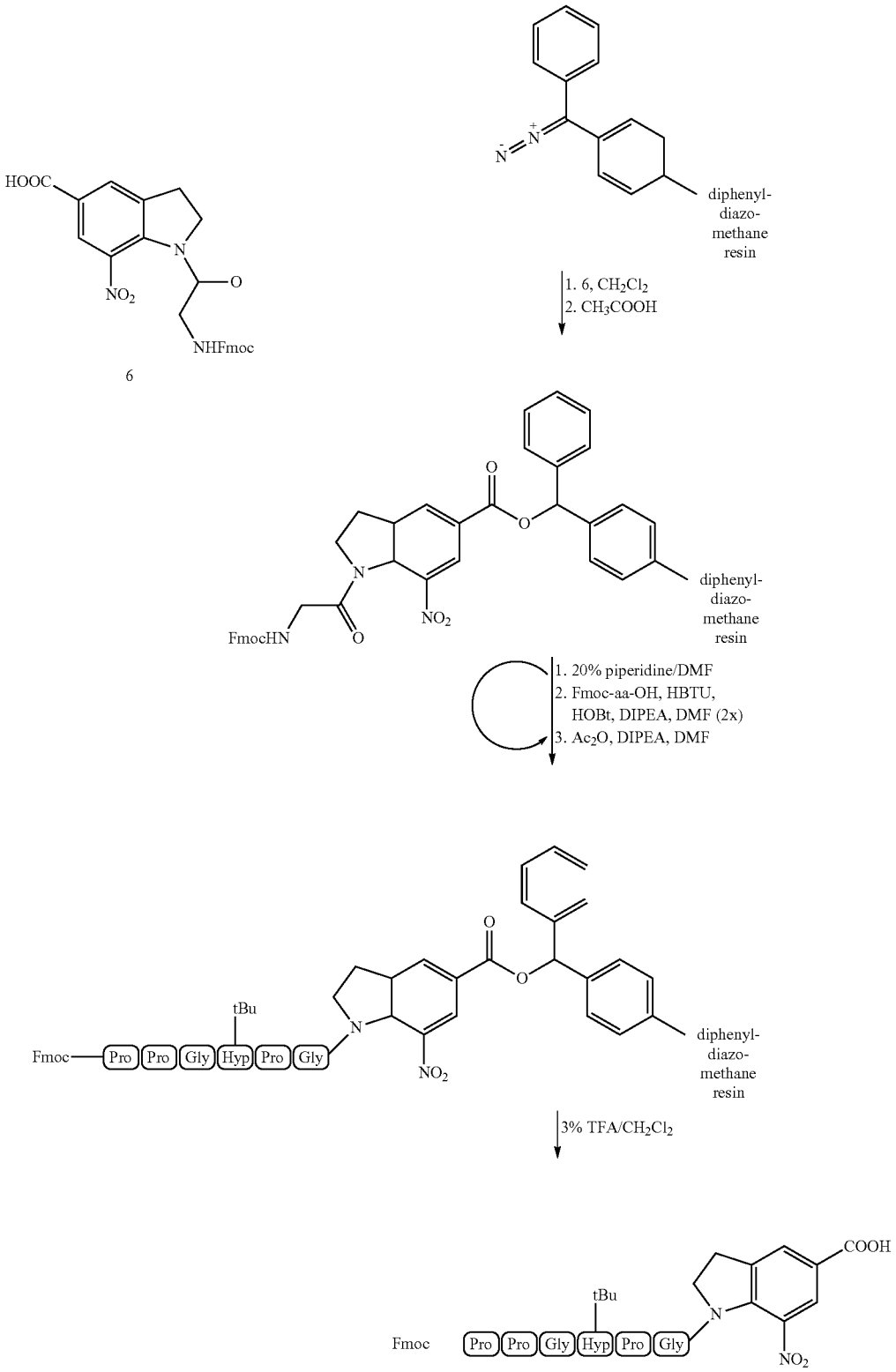

Scheme 3. Synthetic strategy for the preparation of photoreactive peptide 1 by on resin fragment condensation
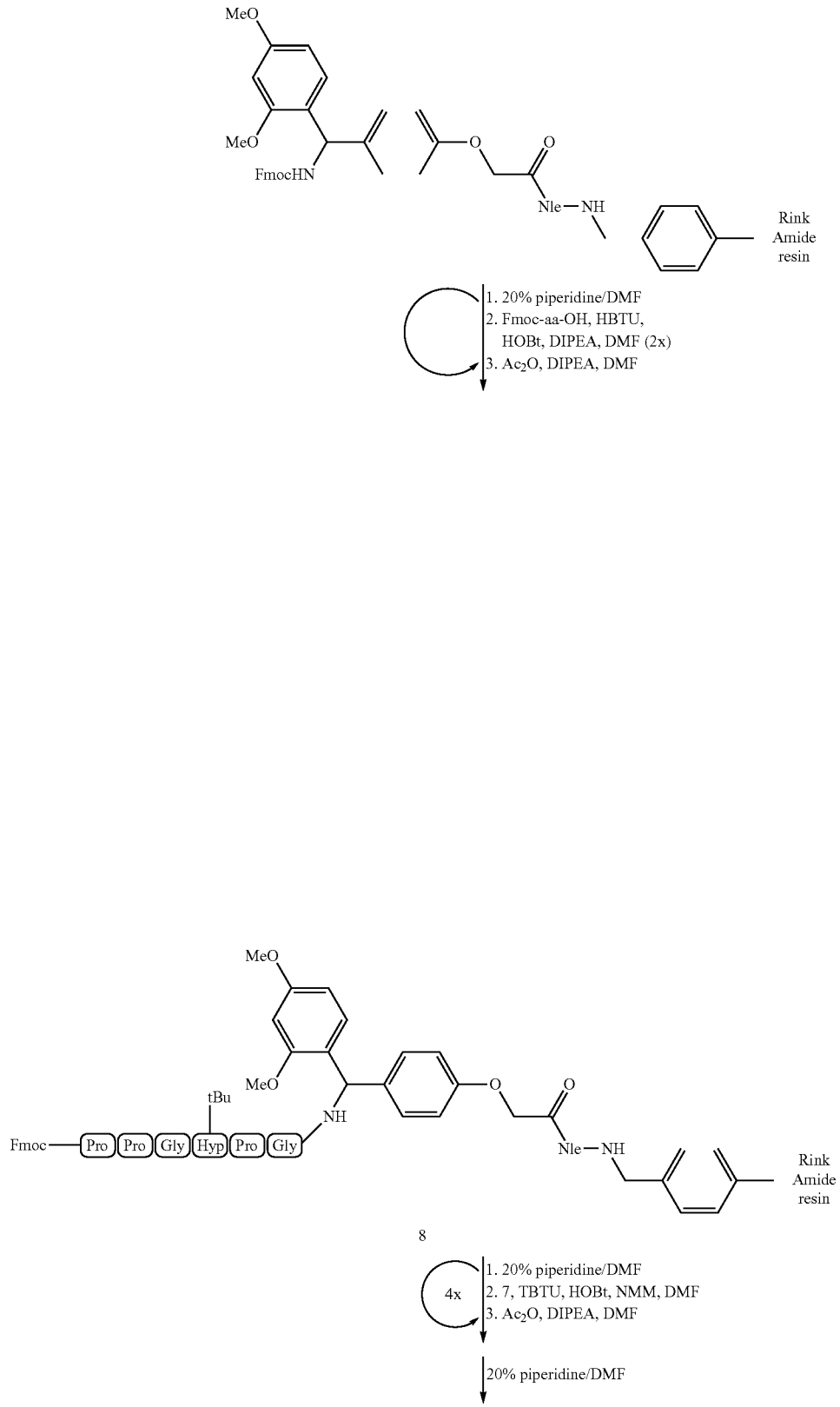

-continued

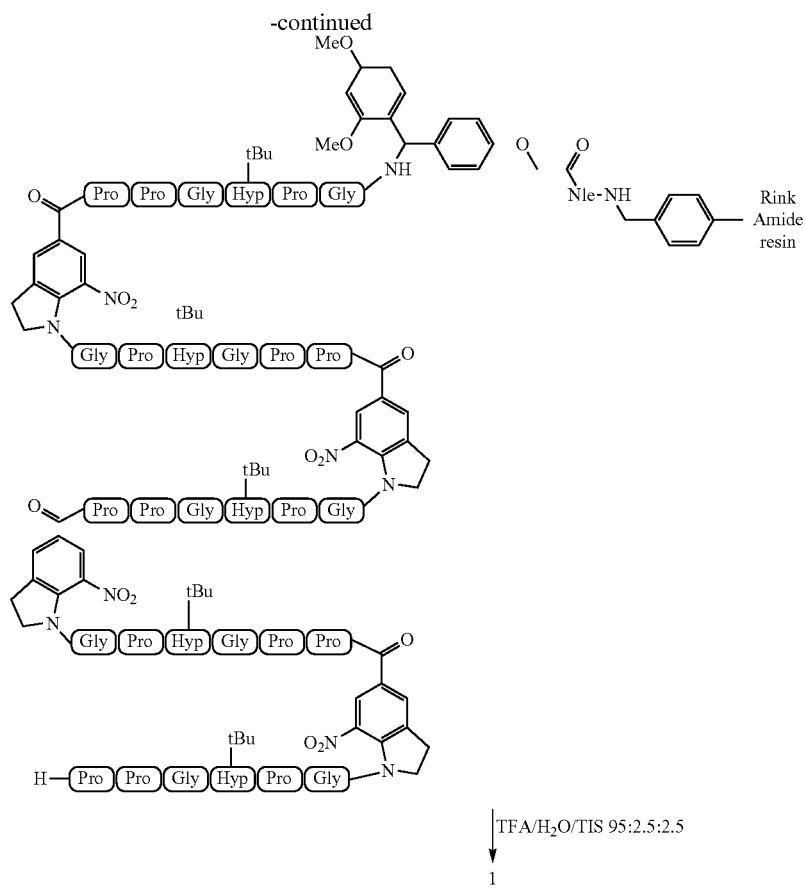

Circular dichroism and thermal stability of peptide 1. In order to study whether or not peptide 1 is capable of undergoing photolysis at 350 nm light irradiation an aqueous solution of 1 was illuminated for 5 min. The mass spectrometric analysis showed that starting material 1 was completely consumed. The three major peaks correspond to the N-terminal (9), middle (10), and C-terminal (11) peptide fragments. Peptide fragments 10 and 11 contain a 7-nitrosoindole moiety, which is in accordance with Corrie's solvent-dependent study (Morrison et al., (2002) *Photochem. Photobiol. Sci.* 1, 960-69). However, a small peak that corresponds to a hexapeptide fragment with a nitroindoline (12) was also observed in this mass spectrum, suggesting that under the reaction conditions photolysis occurred by two pathways, albeit the expected reaction path (Scheme 1, path B) predominated.

Photolysis of N-(Fmoc-glycyl)-5-bromo-7-nitroindoline (13) by a two-photon absorption mechanism. Using the photoreactive amino acid 13 as a model compound the inventors investigated whether its photolysis could be achieved by a two-photon absorption mechanism using a femtosecond laser at 710 nm, and whether N-acyl-7-nitroindolines can undergo localized photolysis within a macroscopic film creating a specific micropattern. The one-photon absorption properties and release of carboxylic acids caged as N-acylated nitroindolines have been reported in the literature (Kaneshiro and Michael, (2006) *Angew. Chem. Int. Ed.* 45, 1077-81; Helgen and Bochet, (2003) *J. Org. Chem.* 68, 2483-86; Nicolaou et al., (2001) *Synlett SI,* 900-03; Joddar et al., (2013) *Biomaterials* 34, 9593-9601). However, the photolysis of N-acylnitroindolines has never been investigated in the context of biopolymers, macroscopic materials, and thin films. After irradiation of a concentrated film of 13 with the femtosecond laser at varying laser powers ranging from 100 mW to 200 mW the formation of orange/brown spots indicates the formation of 5-bromo-7-nitroindoline 14 at the different irradiated sites. The observed color change was the first indication of a successful photolysis (FIG. 10).

Figure 11:
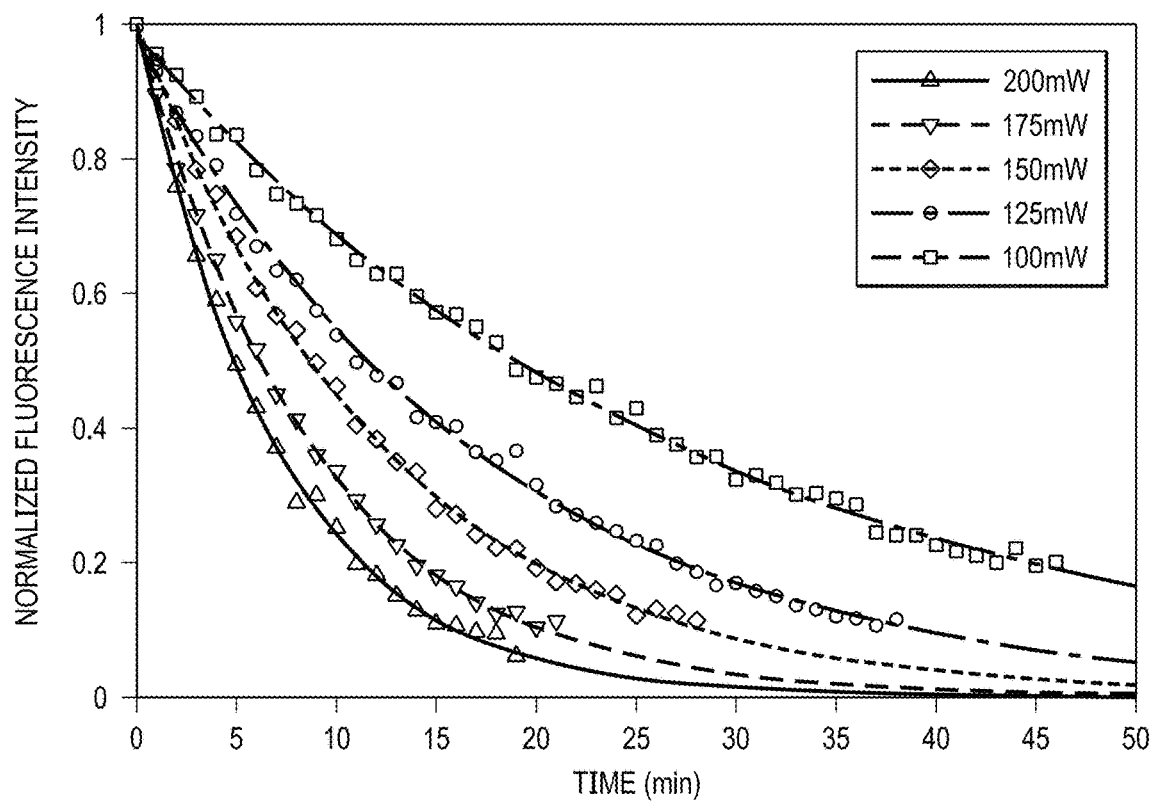
FIG. 11. Fluorescence decay plots of compound 13 with exponential fitting at varying laser power.

Compound 13 exhibits a weak but measurable fluorescence, which is associated with its photochemical conversion into the non-fluorescent compound 14. This unique property was exploited to investigate whether the photolysis occurs by a two-photon absorption mechanism using a fluorescence microscope. All the images produced were collected and analyzed using ImageJ37 to measure the fluorescence intensity of the separate channels. For each irradiated spot, a stack of images was created. An area was chosen within the image and the average fluorescence intensity in each of the green and red channels was recorded. This measurement was recorded in the same region of interest for every image in the stack, each taken one minute apart. A minimum fluorescence threshold was approximated for each image stack, and the fluorescence intensity normalized accordingly. A plot of these normalized intensities over time at varying laser powers from a single sample of 13 is shown in FIG. 11. As can be observed, the kinetics of the photoreaction are proportional to the intensity of the laser as the fluorescence decay is the fastest with the highest laser power (200 mW) and the slowest decay was observed with the weakest laser power (100 mW).

These fluorescence decay plots may be modeled using an exponential decay regression line of the form $F(t)=F_0 e^{-\beta t}$, where $\beta$ is the fluorescence decay rate. This was done using the curve fitting capabilities in Matlab. As mentioned before the fluorescence decay measured is directly proportional to the kinetics of the reaction. Therefore, the fluorescence decay is equal to the rate of the reaction at every specific point and varying laser power. Since this photoreaction is occurring as a result of two-photon absorption, the rate of the reaction is directly proportional to the probability of two-photon absorption as shown in Eq. (1) where I is the excitation laser power.

$$\beta \alpha I^2 \qquad \text{(Eq. 1)}$$

Eq. 1 Probability of two-photon absorption, rate of reaction is proportional to the intensity of the laser squared.

Figure 12:
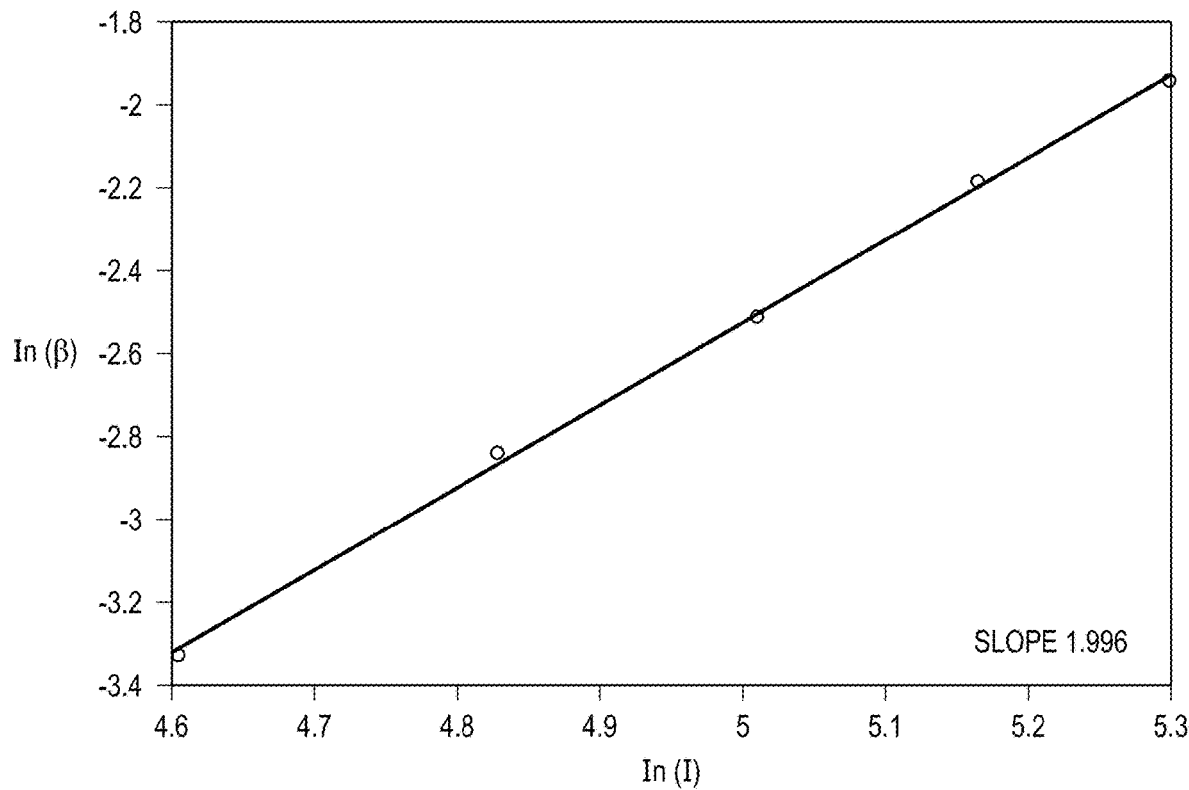
FIG. 12. Double log plot of reaction rate vs. laser intensity for photoreactive compound 13.

Plotting a graph (FIG. 12) where the x axis is the ln(I) and the γ-axis corresponds to the ln(β) for each of the laser intensities employed and their corresponding decay rates produces a linear graph where the slope of the reaction has to be 2 to prove that a two-photon absorption process occurred. After plotting the graph, the slope observed was 1.996 (FIG. 12), which clearly shows that compound 13 was photo-cleaved via a two-photon absorption process.

Figure 10B:
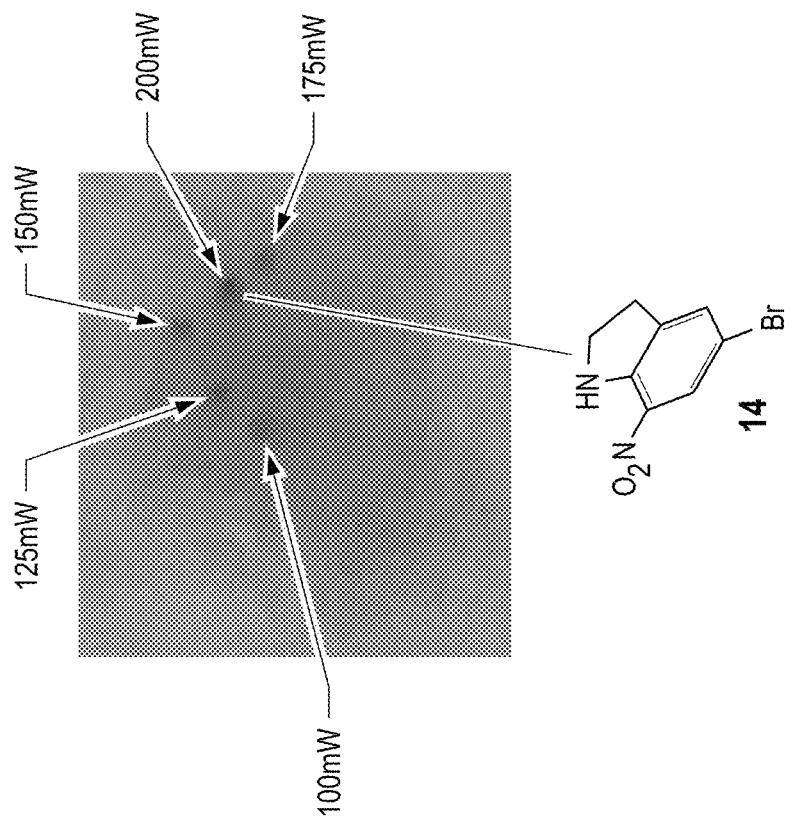
FIGS. 10A-B. Images of a yellow film of N-[fluorenylmethyloxycarbonyl-glycyl]-5-bromo-7-nitroindoline 13 before (A) and after (B) irradiation with a femtosecond laser at 710 nm at several locations with varying laser power (B). The photolysis produces orange/brown colored 5-bromo-7-nitroindoline (14) and colorless fluorenylmethyloxycarbonyl-glycine.
Figure 10A:
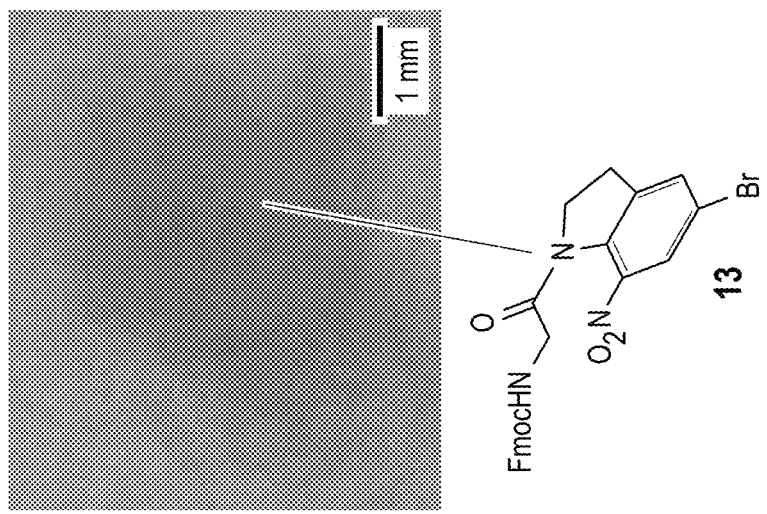

After irradiation the sample shown in FIG. 10b was dissolved and analyzed by HR-ESI-TOF-MS, which showed the formation of 5-bromo-7-nitroindoline 14 (m/z [M+H]+ calcd. 242.9769 and 244.9749, obs. 242.9784 and 244.9765, but not 5-bromo-7-nitrosoindole. The result is in accordance with Corrie's proposed photolysis mechanism of a similar N-acyl-7-nitroindoline in an inert organic solvent that contains only small quantities of water (~1%) (Joddar et al., (2013) *Biomaterials* 34, 9593-9601). Unlike Corries photolysis study in solution, compound 13 was irradiated as a solid film (FIG. 10), however, the film was not anhydrous, and similar to Corries study, it contained sufficient quantities of water to undergo photo hydrolysis corresponding to Scheme 1, path A.

Figure 13:
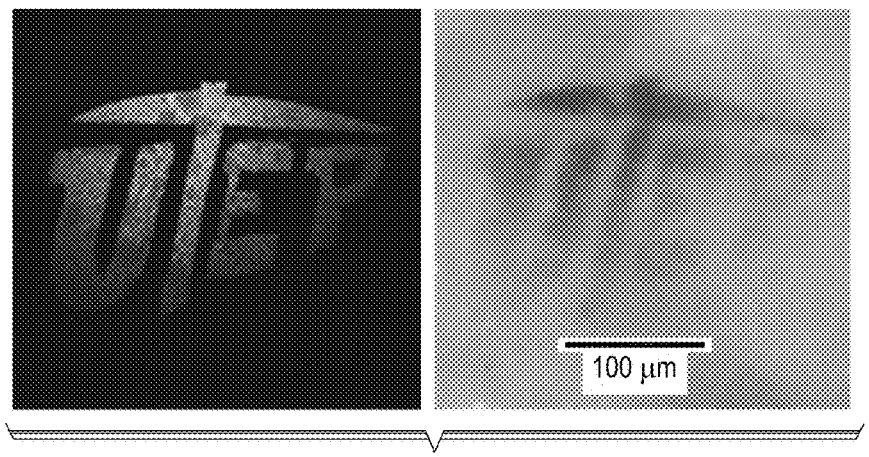
FIG. 13. Left: Fluorescent logo of the University of Texas at El Paso generated by excitation of the photoreactive amino acid 13 with a femtosecond laser at 710 nm through a "UTEP" mask; middle: The letters of the logo underwent photolysis to the non-fluorescent nitroindoline 14. After removal of the mask the background fluoresces; right: UTEP logo under white light.

Generation of a micropattern by two-photon absorption chemistry. In order to demonstrate the suitability of N-acyl-7-nitroindolines for the generation of precise micropatterns using 710 nm femtosecond laser light, a film of compound 13 was illuminated in a pattern with about 10 μm wide features. The illumination occurred through a mask of the logo of the University of Texas at El Paso ("UTEP") in the optical path. This mask was made from a cover glass slip with a dark colored tape; only the UTEP logo, approximately 1 cm wide, was transparent. This mask was placed in the intermediate imaging plane of this microscope, and was further projected onto the sample. Only laser light that passed through the mask reached the film of the photoreactive amino acid 13 in form of the UTEP logo pattern. Initially, the illuminated areas fluoresce (FIG. 13), which triggers the photolysis to the non-fluorescent compound 14. Upon removal of the mask only the background fluoresces, and the UTEP logo appears dark (FIG. 13). When viewed under a regular white light microscope, the yellow background color of compound 13, and the orange/brown color of compound 14 is clearly visible (FIG. 13). The fact that the photolysis of model compound 13 only occurs at sites of illumination, and does not propagate through light-protected areas of the material, suggests that other N-acyl-7-nitroindolines show a similar behavior, and that peptide 1 may be suitable for photolithography and tissue engineering applications.

Figure 14:
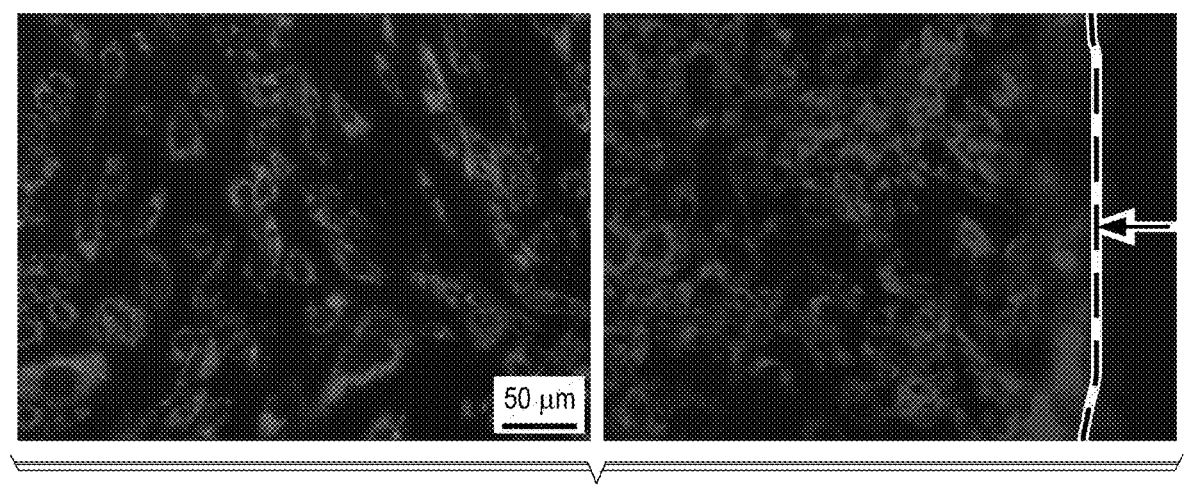
FIG. 14. Human mesenchymal stem cells, pre-stained with PKH26, a cell membrane stain, and seeded atop collagen-like peptide 1 pre-immobilized onto tissue culture grade wells. Left: Images taken from center of the well. Right: cells grew only where the peptide sheet was present.

Cytocompatibility. Whether or not collagen-like peptide 1 is toxic to cells was tested by culturing mesenchymal stem cell on it. FIG. 14 illustrates that peptide 1 is not cytotoxic to the cultured cells as the cells showed viability and confluence within 24 hours of culture. Furthermore, the peptide 1 promoted cell adhesion and migration (arrow in the right image denotes the edge of the immobilized peptide material from where undried/uncoated remnant liquid was aspirated prior to cell seeding. As the rim did not have any of peptide 1 immobilized, cells did not migrate, adhere or proliferate in that area.

B. Materials and Methods

Reagents and Solvents. Fmoc amino acid derivatives were purchased from Anaspec Inc., BACHEM or Chem-Impex Intl. Inc. Diphenyldiazomethane resin and Rink Amide resins were obtained from BACHEM and Novabiochem, respectively. HBTU and TBTU were purchased from Anaspec Inc. and Novabiochem, respectively. HOBt, piperidine, and reserpine were obtained from Sigma Aldrich. Tetrakis(triphenylphosphine) palladium(0), N-methylaniline, N-methylmorpholine, TIS, and tetrachloro-p-benzoquinone were obtained from Acros. 5-Bromo-7-nitroindoline, thionyl chloride, and Ultramark were acquired from Alfa Aesar. Solvents, DIPEA, TFA, and bromophenol blue were obtained from Fisher Scientific. CDCl3 and DMSO-d6 were purchased from Acros and Cambridge Isotope Laboratories, respectively. Thin layer chromatography was performed on silica gel 60 F254 on aluminum (Merck). Column chromatography was performed on silica gel 60, 230-400 mesh from Natland International Corp.

Culture and passaging of human Mesenchymal Stem Cells (MSC). Human adipose derived mesenchymal stem cells were obtained from Lonza at passage=3 (Lonza, Allendale, N.J., USA) and cultured according to manufacturer's recommendations. Certification was obtained and kept in file to ensure that the purchased human MSC (Lonza) was verified to be of the correct lineage and uncontaminated by other cell types or organisms. For the human MSC culture, a complete growth medium (Lonza) specifically MSCGM human Mesenchymal Stem Cell (HMSC) growth BulletKit™ Medium (Lonza) was used for maintaining the mesenchymal stem cells in an undifferentiated state. This medium is referred to as complete growth medium for HMSC here onwards. Prior to cell seeding, T-75 culture flasks were coated with 0.1% gelatin (Sigma Aldrich, St. Louis, Mo., USA) and incubated (37° C., 1 h). After this, the cell suspension in complete culture medium was transferred to a gelatin coated T-75 flask and incubated for 1 h (37° C., 5% CO2 and 95% RH). Prior to cell culture, the gelatin solution used for coating of the flasks was aspirated. After 70% confluency in culture was attained, cells were trypsinized and passaged for further experiments. Normal morphology and phenotype of the cultured cells were compared with other's published images of human MSC (Ball, Shuttleworth et al. 2004). Cells were pre-stained with PKH26 a red fluorescent membrane staining dye (Sigma) following manufacturer's protocols.

Instrumentation. Peptides were synthesized semi-automatically using a Tribute peptide synthesizer from Protein Technologies, Inc. (USA). Reversed phase chromatography was performed on a Fast Protein Liquid Chromatography system in an AKTA Purifier from GE Healthcare Life Sciences. Superfrost microscope slides were obtained from Fisher Scientific (USA). UV-VIS absorption spectra were measured on a Shimadzu UV-3101PC UV-VIS-NIR scanning spectrophotometer and quartz cuvettes of 1 cm path length were used. Fluorescence spectra were measured on a Shimadzu RF-6000 spectrofluorophotometer using a standard quartz cuvettes of 1 cm path length and the Raman scattering of the solvent was subtracted. 1H NMR and 13C NMR were recorded on a JEOL ECA-600 (600 MHz) or a Bruker Avance III HD (400 MHz). Mass spectrometry was performed on a high resolution JEOL Accu TOF mass spectrometer using an Electrospray Ionization source and a High Resolution QExactive Plus-mass spectrometer. The photolysis of peptide 1 in aqueous solution was performed in a Rayonet RPR200 photochemical reactor (USA) equipped with 16 UV lamps (350 nm) producing approximately $1.6 \times 10$ photons/sec/cm$^3$. Far-UV Circular Dichroism (CD) studies were conducted using a Jasco-1500 spectropolarimeter connected to a Peltier temperature controller.

Laser set-up. The details of in-housed developed videorate two-photon microscope was previously described (Joddar et al., (2013) Biomaterials 34, 9593-9601). The light source is a mode-locked Ti:Sapphire laser (Maitai HP, 690-1040 nm, 100 fs, 80 MHz, Newport, Santa Clara, Calif.). The inventors have used 710 nm light to achieve two-photon excitation of N-acyl-nitroindoline moieties. The home-built x-y scanner (polygon, galvanometer) has a 30 frames/s scanning rate. The laser power at the sample site is varied by rotating a half-wave plate in front of a polarizer. The fluorescence signal from the sample are detected in three spectral channels with photomultiplier tubes (PMTs, R3896, Hamamatsu, USA): red (570-616 nm, FF01-593/46, Semrock, USA), green (500-550 nm, FF03-525/50, Semrock, USA), and blue (417-477 nm, FF02-447/60, Semrock, USA). The outputs of these three PMTs are fed into red/green/blue channels of a frame grabber (Solios eA/XA, Matrox, Quebec, Canada). Two-dimensional images in the x-y plane are acquired through a home-built software program. Each frame has 500×500 pixels. Each final static image is an average of 30 frames. In the UTEP logo written experiment a photomask was placed at the intermediate image plane in the optical path, and the logo pattern was projected onto the objective lens focal plan to partially block the illumination light for pattern formation.

Synthesis. Photoreactive Peptide 1. The photoreactive peptide 1 was synthesized from hexapeptide 8, which was elongated by repeated coupling of pre-prepared peptide 7 by on resin fragment condensation. Hexapeptide 8 was synthesized on Rink Amide resin (loading capacity 0.62 mmol/g). The resin (0.06 mmol, 0.10 g) was swollen in DCM (3 mL) for 30 min and washed 5× with DMF. A solution of 20% piperidine in DMF (3 mL) was added and the mixture shaken for 15 min, then washed with DMF (5×10 mL). Fmoc-Gly-OH (0.06 mmol, 0.02 g, 1 eq.), HBTU (0.06 mmol, 0.02 g), HOBt (0.06 mmol, 0.01 g) and DIPEA (0.12 mmol, 0.02 mL) were dissolved in DMF (0.12 M, 0.50 mL), immediately added to the resin and mixed for 45 min, which purposefully achieved a reduced loading of 75% based on the quantification of dibenzofulvene upon Fmoc removal of the first amino acid. An incomplete loading was desired in order to minimize peptide aggregation. Capping was accomplished after each coupling with 10% Ac2O, 5% DIPEA in DMF (3 mL, 15 min). The next five amino acids (Fmoc-Pro-OH, Fmoc-Hyp(tBu)OH, Fmoc-Gly-OH, Fmoc-Pro-OH, and Fmoc-Pro-OH) were coupled by dissolving 5 equiv. of the Fmoc-AA-OH, HBTU, HOBt and 10 eq. of DIPEA in DMF (0.30 M), which was added to the resin, stirred for 15 min, double coupled and capped, to furnish the resin-bound hexapeptide 8. Following removal of Fmoc, the peptide was further elongated by peptide fragment condensation (4×) with the photoreactive hexamer 7 to obtain 1 (Scheme 3). A solution of 7 (0.06 mmol, 0.06 g, 2.5 eq.), O-(Benzotriazol-1-yl)-N,N,N',N'-tetramethyluronium tetrafluoroborate (TBTU, 0.06 mmol, 0.02 g), HOBt (0.06 mmol, 0.01 g), and N-methylmorpholine (NMM 0.12 mmol, 0.01 mL) in N-methylpyrrolidone (NMP) (0.10 M, 0.60 mL) was added to the solid supported peptide 8 containing a liberated amine. This suspension was stirred for 9-11 hours and carefully monitored by bromophenol blue and chloranil test. The resin was capped with the previously mentioned capping reagent. This cycle was performed a total of four times to elongate the peptide to completion. A crude photoreactive CMP 1 was liberated from the dry resin by standard cleavage and global deprotection conditions (95% TFA, 2.5% triisopropylsilane (TIS), 2.5% water, 5 mL, 3 hrs.) and the resin was washed twice with clean TFA. The crude peptide was concentrated under vacuum to a glassy film and precipitated in cold diethyl ether. The solution was centrifuged and the mother liquor was removed by decantation. The crude peptide was washed several times with cold diethyl ether and finally lyophilized in water. The crude peptide 1 was dissolved in water (HPLC grade) and pre-purified by size exclusion chromatography by isocratic elution with water (90 cm. long column, Superdex, flow rate 0.3 mL/min). Final purification (48%) was achieved on a XK26 Source column packed with (C18) and a gradient of 10-35% (2% CH3CN, and 0.1% TFA in H$_2$O (solvent A), 85% CH3CN, and 0.1% TFA in H$_2$O (Solvent B)) in 10 CV. The desired photoreactive CMP 1 was then confirmed by ESI TOF-MS (positive mode) m/Z observed 1685.7186 ([M+2H]2+ calcd. 1685.7205), 1124.4830 ([M+3H]3+ calcd. 1124.4839). The normalized absorption pectrum of this compound in water (HPLC grade) ($2.97 \times 10^{-5}$M) exhibits two absorption region maxima located at 251 and 332. The fluorescence emission spectra of this compound in water (HPLC grade) ($2.97 \times 10^{-5}$M) was recorded in the wavelength range of 333-750 nm and excited by 332 nm exhibiting an emission maximum of 397 nm.

N-(Fmoc-glycyl)-5-carboxylic acid-7-nitroindoline 6. The photoreactive glycine building block 6 suitable for SPPS was synthesized from nitroindoline derivative 1211 by Pd(0) catalyzed deallylation (Acosta et al., (2014) *Biomed. Opt. Express* 5, 3990-4001) (Scheme 5). In a round bottom flask, 12 (1.15 mmol, 0.61 g) and tetrakis(triphenylphosphine)palladium (0.12 mmol, 0.13 g) were dissolved in anhydrous tetrahydrofuran (THF, 10 mL) under argon. N-methylaniline (11.50 mmol, 1.25 mL) was added to the solution which immediately turned dark red. The reaction was monitored by TLC until the starting material was consumed (1 h). THF was removed under reduced pressure and the remainder was dissolved in ethyl acetate and washed extensively with a 1M HCl solution (10×50 mL), followed by water (5×50 mL), brine (2×50 mL) and dried over magnesium sulfate. Ethyl acetate was removed under reduced pressure to obtain an orange solid (0.56 g, quantitative) and no further purification was required. RF=0.18 (MeOH/DCM 5:95). 1H NMR (400 MHz, 295 K, DMSO-d6) δ 13.44 (s, 1H, COOH); 8.10 (s, 1H, Ind-H6); 8.08 (s, 1H, Ind-H4); 7.90 (d, 2H, 3J=7.4 Hz, Fmoc-ArH); 7.78 (t, 1H, NH); 7.75 (d, 2H, Fmoc-ArH); 7.42 (t, 2H, Fmoc-ArH); 7.34 (t, 2H, Fmoc-ArH); 4.33-4.30 (m, 4H, Fmoc-CH2, Ind-H2, H2'); 4.25 (t, 1H, 3JFmocCH-FmocCH2=7.0 Hz, Fmoc-CH); 4.10 (d, 2H, 3JHα/NH=6.0 Hz, Hα, Hα$^3$); 3.29 (t, 2H, 3JInd-H2/Ind-H2=8.1 Hz, Ind-H3) ppm; 13C NMR (100 MHz, 295 K, DMSO-d6) δ 168.2, 156.4, 143.8, 140.7, 139.3, 137.6, 136.5, 129.3, 127.6, 127.0, 125.2, 123.4, 120.0, 65.7, 48.8, 46.6, 43.6, 28.3 ppm. ESI-TOF-MS m/z calcd: 486.1301 [M−H]−; obs.: 486.1327. The normalized absorption spectrum of this compound in DCM ($4.11 \times 10^{-5}$M) exhibits three absorption region maxima located at 268, 301 and 324 nm. The fluorescence emission spectra of this compound in DCM ($8.21 \times 10^{-5}$ M) was recorded in the wavelength range of 326-750 nm and excited by 324 nm exhibiting an emission maximum of 392 nm.

Scheme 4.
Synthesis of the photoreactive amino acid building block 6: (a) SOCl2, toluene, 70° C.; (b) Pd(PPh3)4, N-methylaniline, THF.

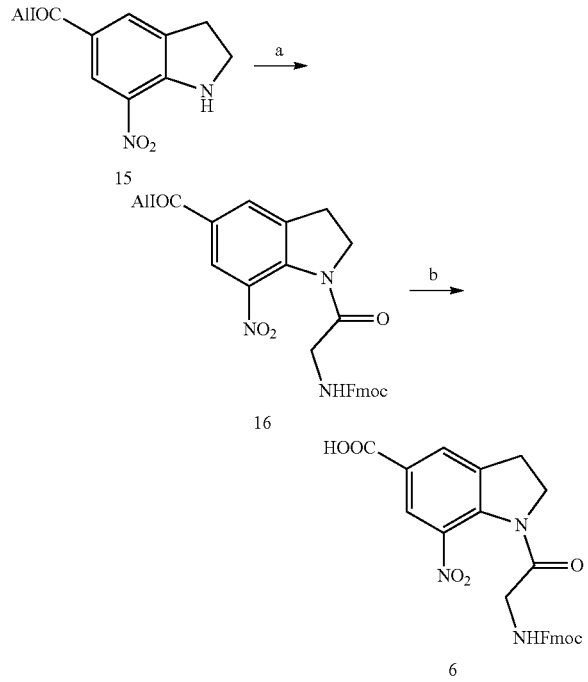

Photoreactive peptide 7. The photoreactive amino acid 6 served as one of the building blocks for the SPPS of the heptamer peptide acid 7 (Scheme 2), needed for the synthesis of the full length photoreactive peptide 1. Diphenyldiazomethane resin (loading capacity 0.7 mmol/g) (0.99 mmol, 1.42 g) was swollen in 10 mL of DCM in a peptide synthesis vessel for 20 min. Compound 6 (1.0 mmol, 0.49 g) was dissolved in a DCM:DMF (2:1) mixture (0.20 M, 5 mL) and added to the resin and shaken for 5 hours in a peptide synthesizer. Upon completion of the coupling, the excess of compound 6 was recovered. The inventors used only ~1 equiv. of the first amino acid in order to accomplish a reduced loading to minimize peptide aggregation on the resin. The resin was suspended in 5 mL of glacial acetic acid for 1 hour to cap the remaining diphenyldiazomethane sites. A piperidine in DMF solution (20%) was added (5 mL) and stirred for 15 min. The amount of resin loading was determined to be 47% by the spectrophotometric quantification of dibenzofulvene at 290 nm, ε5253. Fmoc-Pro-OH (5.0 mmol, 1.68 g), N,N,N',N'-tetramethyl-O-(1H-benzotriazol-1-yl) uronium hexafluorophosphate (HBTU) (5.0 mmol, 1.90 g) and 1-hydroxybenzotriazole hydrate (HOBt) (5 mmol, 0.68 g) were dissolved in DMF (1 M, 5 mL) and N,N-diisopropylethylamine (DIPEA) (10 mmol, 1.75 mL) was added just before the solution was added to the resin. The vessel was shaken for 15 min, followed by NMP washings (5×5 mL) and double coupling of the amino acid was performed (15 min). Any free amino groups potentially still present were capped with 10% Ac2O and 5% DIPEA in DMF (5 mL, 10 min). The synthetic cycle was repeated for each amino acid of the heptamer. Every coupling was monitored until completion through the bromophenol blue and chloranil tests. The latter is preferred for N-terminal proline. The peptide was cleaved from the resin with a 3% trifluoroacetic acid (TFA) solution in DCM (10 mL) for 3 min with 15 repetitions. The acidic solution was concentrated to approximately 5 mL and it was quickly transferred dropwise to cold diethyl ether to obtain a yellow precipitate of a fully protected photoreactive hexamer 7. The suspension was centrifuged and the supernatant decanted. It was then washed several times with cold diethyl ether followed by lyophilization in benzene. The crude peptide was purified by silica gel flash chromatography (gradient of 5% MeOH to 10% MeOH in DCM) to isolate 7 (0.38 g) in 81% yield based on the loading of the first amino acid. Rf=0.1 (MeOH/DCM 5:95). HR-ESI-TOF-MS m/z calcd.: 1005.4358 [M+H]+; obs.: 1005.4334; m/z calcd.: 1027.4178 [M+Na]+; obs. 1027.4176. The normalized absorption spectrum of this compound in DCM ($9.95 \times 10^{-5}$ M) exhibits two absorption region maxima located at 267 and 327 nm. The fluorescence emission spectra of this compound in DCM ($9.95 \times 10^{-5}$ M) was recorded in the wavelength range of 330-750 nm and excited by 327 nm exhibiting an emission maximum of 391 nm.

N-Fmoc-glycyl-5-bromo-7-nitroindoline 13. This photoreactive amino acid was synthesized by acylation of commercially available 5-bromo-7-nitroindoline with an Fmoc protected glycine chloride generated in situ using a procedure similar to a published method [20]. In a dry and argon flushed round bottom flask, 5-bromo-7-nitroindoline (2.00 mmol, 0.49 g, 1 eq.) and Fmoc-Gly-OH (3.00 mmol, 0.89 g) were suspended in anhydrous toluene (10 mL). The suspension was placed in a 70° C. oil bath and stirred for 15 minutes. Thionyl chloride (8.00 mmol, 0.58 mL) was then added dropwise and the reagents went into solution over a period of 30 minutes. The reaction was monitored by TLC until near complete consumption of limiting reagent (24 hrs.) The solution was then diluted with ethyl acetate (250 mL) and washed with sodium bicarbonate (3×150 mL), water (3×150 mL) and brine (2×100 mL). The organic layer was dried over anhydrous magnesium sulfate, filtered and concentrated under reduced pressure to obtain an orange crude solid. 9 was isolated by silica column chromatography (EtOAc:Hex 1:1) (90%, 0.94 g). Rf 0.18 (EtOAc:Hex 1:2); 1H NMR (600 MHz, 295 K, CDCl3) δ 7.76 (s, 1H, Ind-H6); 7.75 (d, 2H, 3J=7.5 Hz, Fmoc-ArCH); 7.59 (d, 2H, 3J=7.5 Hz, Fmoc-ArCH); 7.53 (s, 1H, Ind-H4); 7.38 (t, 2H, 3J=7.5 Hz, Fmoc-ArCH); 7.29 (t, 2H, 3J=7.5 Hz, Fmoc-ArCH); 5.82 (t, 1H, NH); 4.36 (d, 2H, 3JFmocCH2-FmocCH=7.2 Hz, Fmoc-CH2); 4.22-4.17 (m, 5H, α-CH2, Ind-H2, Fmoc-CH); 3.22 (t, 2H, 3JIndH3-IndH2=8.0 Hz, Ind-H3). 13C NMR (150 MHz, 295 K, CDCl3) 67 C 167.3, 156.7, 144.0, 141.6, 141.1, 138.7, 133.5, 132.2, 128.0, 127.4, 125.8, 125.5, 120.3, 117.4, 67.6, 49.1, 47.3, 44.5, 29.2. HR-ESI-TOF-MS (positive) observed 539.0904 and 541.0937 ([M+NH4]+ calculated 539.0930 and 541.0913), 544.0489 and 546.0463 ([M+Na]+ calculated 544.0484 and 546.0467). The normalized absorption spectrum of this compound in HPLC grade chloroform ($7.66 \times 10^{-5}$ M) exhibits two absorption region maxima located at 257 and 342 nm. The fluorescence emission spectra of this compound in HPLC grade chloroform ($2.37 \times 10^{-5}$ M) was recorded in the wavelength range of 280-750 nm and excited by 342 nm exhibiting an emission maximum of 383 nm.

Allyl N-(Fmoc-glycyl)-5-carboxylate-7-nitroindoline (16). 5-Allyl carboxylate-7-nitroindoline 15 11 was reacted with Fmoc-Gly-OH in the presence of thionyl chloride similar to a reported procedure (Pass et al., (1981) J. Am. Chem. Soc. 103, 7674-75) to produce the fully protected derivative 16. In a dry and argon flushed round bottom flask, Fmoc-Gly-OH (4.00 mmol, 1.19 g) and 15 (2.00 mmol, 0.50 g, 1 equiv.) were suspended in anhydrous toluene (15 mL) and warmed up to 70° C. Thionyl chloride (10.00 mmol, 0.73 mL) was added dropwise, after 60 min a clear solution was obtained. The reaction was monitored by TLC until the limiting reagent was almost consumed (40 h). The solution was diluted with ethyl acetate (200 mL) and washed with sodium bicarbonate (3×100 mL), water (3×100 mL) and brine (2×100 mL). The organic layer was dried over anhydrous magnesium sulfate, filtered and concentrated under reduced pressure to obtain an orange solid. Product 12 was purified by silica column chromatography (EtOAc:Hex 2:1) (93%, 0.98). Rf=0.13 (EtOAc:hexanes 1:1). 1H NMR (600 MHz, 296 K, CDCl3) δ H 8.34 (s, 1H, Ind-H6); 8.08 (s, 1H, Ind-H4); 7.75 (d, 2H, 3J=7.5 Hz, Fmoc-ArH); 7.59 (d, 2H, 3J=7.5 Hz, Fmoc-ArH); 7.38 (t, 2H, 3J=7.5 Hz, Fmoc-ArH); 7.36 (s, residual benzene); 7.30 (t, 2H, 3J=7.5 Hz, Fmoc-ArH); 6.06-5.99 (m, 1H, all-CH2=CH); 5.81 (t, 1H, NH); 5.43-5.40 (dd, 1H, 2JallCH2-allCH2'=17.2 Hz, 3JallCH2'-allCH=1.3 Hz, all-CH2=CH); 5.33-5.31 (dd, 1H, 2JallCH2'-allCH2=17.0 Hz, 3JallCH2'-allCH=1.1 Hz, all-CH2'=CH); 4.84 (d, 2H, 3JallCH2-allCH=5.2 Hz, all-CH2); 4.37 (d, 2H, 3JFmocCH2-FmocCH=6.9 Hz, Fmoc-CH2); 4.28 (t, 2H, 3JIndH2-IndH3=8.1 Hz, Ind-H2); 4.22-4.19 (m, 3H, Fmoc-CH, α-CH2); 3.29 (t, 2H, 3JIndH3-IndH2=8.1 Hz, Ind-H3). 13C NMR (600 MHz, 296 K, CDCl3) δ C 167.33, 163.94, 156.34, 143.69, 141.22, 140.12, 137.52, 136.71, 131.61, 129.36, 128.31 (residual benzene), 127.70, 127.19, 127.08, 125.11, 124.95, 119.95, 119.09, 67.33, 66.28, 49.02, 46.99, 44.32, 28.68. HR-ESI-TOF-MS (positive) observed 550.1597 ([M+Na]+ calculated 550.1590), 566.1332 ([M+K]+ calculated 566.1330). The normalized absorption spectrum of this compound in DCM ($3.79 \times 10^{-5}$ M) exhibits three absorption region maxima located at 258, 267 and 324 nm. The fluorescence emission spectra of this compound in DCM ($7.59 \times 10^{-5}$ M) was recorded in the wavelength range of 335-750 nm and excited by 324 nm exhibiting an emission maximum of 390 nm.

Circular Dichroism (CD) of peptide 1 and thermal stability measurements. Far-UV CD studies were conducted to study the secondary structure of peptide 1. The measurements were carried out using a 20 μM solution of the lyophilized peptide 1 in 15 mM NaCl and 10 mM Na/K buffer (pH 6.8). The sample was placed into a quartz cuvette of 1 mm path length (Jasco) and heated from 20° C.-70° C. to characterize its thermal stability. At each temperature, the sample was equilibrated for 4 min prior measurement of the spectrum. CD scans were performed at a range from 196-240 nm with three accumulations of data at each temperature to improve the S/N ratio. Each spectrum underwent 11 point Savitzky-Golay smoothing to minimize high frequency noise. The experimentally estimated ellipticities (Gobs) were converted to mean molar ellipticity [θ] using the formula: [θ]=(θobs)/ncl where l is the path length of the cuvette; c is the concentration of the peptide, and n is the number of stereogenic centers in the peptide.

Photolysis of an aqueous solution of peptide 1 at 350 nm. The photoreactive peptide 1 (2 mg) was dissolved in 2 mL of HPLC grade water (pH 7.3; 0.29 mM), placed into a plastic microcentrifuge tube and irradiated with ultraviolet light at 350 nm in a Rayonet photoreactor for 5 min at room temperature, followed by mass spectrometric analysis of the crude reaction mixture.

Two-photon excitation and photo-cleavage of N-Fmoc-glycyl-5-bromo-7-nitroindoline 13. The photoreactive amino acid 13 (2 mg) was dissolved in 2 μL DMF to give a 1.92 M solution which was placed on a microscope slide. The solution was left to dry at room temperature in the dark for 30 min affording an approximately 70 μm thick film of compound 9. The sample was covered with a coverslip and immediately used for the photolysis experiment. Several spots within the sample were chosen for irradiation with the femtosecond laser at 710 nm, and each spot was irradiated with a specific excitation laser power (100 mW, 125 mW, 150 mW, 175 mW, or 200 mW). Upon excitation, the photoreactive amino acid 9 emits a weak fluorescence, which was collected using a combination of red and green photomultiplier tubes. The excitation triggers the photolysis of the glycine's amide bond, producing non-fluorescent Fmoc-glycine and 5-bromo-7-nitroindoline (10). As the photolysis progresses, the number of fluorescent molecules decreases, and consequentially a decrease in average fluorescence intensity at the irradiation site is measured. An image was taken every minute at each location and the fluorescence profile was tracked throughout the reaction. The location of each irradiated spot was recorded before a new spot was irradiated with a new laser excitation power.

Mesenchymal stem cell growth on the photoreactive peptide. For testing the cytocompatibility of the purified peptide 1, ~1 mg was dissolved in 100 μL of distilled water and coated atop 24 wells of a tissue culture treated polystyrene dish and dried under a sterile laminar flow hood for 10-15 min prior to culture. Following this, cells were seeded atop this layer and cultured for 24 hours after which they were imaged using fluorescence microscopy (Zeiss Axiovision).

C. Conclusion

A photoreactive 30mer collagen-like peptide with four photoreactive N-peptidyl-7-nitroindoline moieties was synthesized and its photochemical and photophysical properties were studied. The temperature dependent circular dichroism spectra of this peptide provide the evidence of its folding into a triple helix similar to other collagen-mimicking peptides reported in the literature, and show an unusual structural stability. The four units of the unnatural amino acid 5-carboxylic acid-7-nitroindoline in the peptide sequence may partially contribute to this stability of its secondary structure. When an aqueous solution of the photoreactive peptide is irradiated at 350 nm, photolysis occurs at all photoreactive amide bonds producing the expected peptide segments. A photoreactive N-glycyl-7-nitroindoline model compound was used to study its ability to undergo photolysis by a two-photon absorption mechanism using a femtosecond laser at 710 nm. A concentrated film of this photoreactive amino acid was irradiated at precise locations producing well-resolved micropatterns. These results suggest that the photoreactive collagen-like peptide may be a new biomimetic material that can be structurally manipulated with UV light or femtosecond laser photolysis. Mesenchymal stem cells were able to grow on a surface coated with this photoreactive peptide in culture medium showing that this peptide is not toxic to cells. All together these data suggest that photoreactive collagen-like peptides can serve as novel matrices whose macroscopic structure can be photochemically manipulated at the microscale, which could guide cell growth in distinct patterns (Joddar et al., (2013) Biomaterials 34, 9593-9601).

ABBREVIATIONS

DCM, dichloromethane); DIPEA, N,N,N-diisopropylethylamine; ESI, electrospray ionization; HBTU, N,N,N',N'-

Tetramethyl-O-(1H-benzotriazol-1-yl)uronium hexafluorophosphate; HOBt, hydroxybenzotriazole; HR, high resolution; MSC, mesenchymal stem cells; NMR, nuclear magnetic resonance); SPPS, solid phase peptide synthesis; TBTU, 0-(Benzotriazol-1-yl)-N,N,N',N'-tetramethyluronium tetrafluoroborate; TFA, trifluoroacetic acid; TIS, triisopropylsilane; TLC, thin layer chromatography; TOF, time of flight; UV-VIS, ultraviolet-visible.

What is claimed is:

1. A bifunctional cross-linking agent comprising:
   a N-acyl-7-nitroindoline moiety selected from the group consisting of a thiocarbamate of N-acyl-7-nitroindoline, a thiocarbamate of N-acyl-7-nitro-5-phenyl-nitroindoline, and combinations thereof,
   wherein the N-acyl-7-nitroindoline moiety further comprises at least two reactive groups for crosslinking capability of biopolymers,
   wherein the at least two reactive groups further comprise a first reactive moiety and a second reactive moiety.

* * * * *

UNITED STATES PATENT AND TRADEMARK OFFICE
CERTIFICATE OF CORRECTION

| | |
|---|---|
| PATENT NO. | : 11,370,757 B2 |
| APPLICATION NO. | : 17/074232 |
| DATED | : June 28, 2022 |
| INVENTOR(S) | : Michael et al. |

It is certified that error appears in the above-identified patent and that said Letters Patent is hereby corrected as shown below:

In the Specification

Replace Column 1, Lines 17-22 with the following:
This invention was made with government support under grant numbers DBI-1429708, and DMR-1205302 awarded by the National Science Foundation; and grant numbers 1SC2GM103719, RL5GM118969, TL4GM118971, and UL1GM118970 awarded by the NIGMS National Institutes of Health. The government has certain rights in the invention.

Signed and Sealed this
Twenty-third Day of May, 2023

Katherine Kelly Vidal
*Director of the United States Patent and Trademark Office*